United States Patent
Thévenin et al.

(10) Patent No.: US 11,312,737 B2
(45) Date of Patent: Apr. 26, 2022

(54) AMIDE-LINKED EP4 AGONIST-BISPHOSPHONATE COMPOUNDS AND USES THEREOF

(71) Applicant: SIMON FRASER UNIVERSITY, Burnaby (CA)

(72) Inventors: Marion Thévenin, Haubourdin (FR); Robert N. Young, Vancouver (CA); Gang Chen, Langley (CA)

(73) Assignee: SIMON FRASER UNIVERSITY, Burnaby (CA)

( * ) Notice: Subject to any disclaimer, the term of this patent is extended or adjusted under 35 U.S.C. 154(b) by 0 days.

(21) Appl. No.: 16/518,132

(22) Filed: Jul. 22, 2019

(65) Prior Publication Data

US 2019/0345179 A1 Nov. 14, 2019

Related U.S. Application Data

(63) Continuation of application No. 15/735,372, filed as application No. PCT/IB2016/053482 on Jun. 13, 2016, now Pat. No. 10,400,000.

(60) Provisional application No. 62/175,118, filed on Jun. 12, 2015.

(51) Int. Cl.
| | | |
|---|---|---|
| *C07F 9/572* | (2006.01) | |
| *C07F 9/38* | (2006.01) | |
| *A61K 47/54* | (2017.01) | |
| *A61P 19/08* | (2006.01) | |

(52) U.S. Cl.
CPC ............ *C07F 9/572* (2013.01); *A61K 47/548* (2017.08); *A61P 19/08* (2018.01); *C07F 9/3873* (2013.01)

(58) Field of Classification Search
CPC .................................. C07F 9/572; C07F 9/38
See application file for complete search history.

(56) References Cited

U.S. PATENT DOCUMENTS

| | | | |
|---|---|---|---|
| 3,224,995 A | 12/1965 | Pree | |
| 4,320,136 A | 3/1982 | Scribner | |
| 4,922,007 A | 5/1990 | Kieczykowski et al. | |
| 5,019,651 A | 5/1991 | Kieczykowski et al. | |
| 5,409,911 A | 4/1995 | Tyler et al. | |
| 5,510,517 A | 4/1996 | Dauer et al. | |
| 5,648,491 A | 7/1997 | Dauer et al. | |
| 6,121,253 A | 9/2000 | Han et al. | |
| 7,109,223 B2 | 9/2006 | Han et al. | |
| 7,238,710 B2 | 7/2007 | Han et al. | |
| 7,772,392 B2 * | 8/2010 | Old ..................... | C07D 403/06 540/200 |
| 9,150,537 B2 * | 10/2015 | Maruyama .............. | A61P 27/06 |
| 9,611,284 B2 | 4/2017 | Billot et al. | |
| 9,650,414 B1 | 5/2017 | Young et al. | |

| | | |
|---|---|---|
| 2005/0239872 A1 | 10/2005 | Billot et al. |
| 2006/0258726 A1 | 11/2006 | Billot et al. |
| 2013/0157984 A1 | 6/2013 | Young et al. |

FOREIGN PATENT DOCUMENTS

| | | |
|---|---|---|
| CA | 2648159 A1 | 10/2007 |
| EP | 855389 A2 | 7/1998 |
| EP | 1114816 A1 | 7/2001 |
| EP | 1132086 A2 | 9/2001 |
| EP | 2465506 A1 | 6/2012 |
| EP | 2576575 A1 | 4/2013 |
| JP | S60034971 A | 2/1985 |
| JP | 2013531627 A | 8/2013 |
| WO | 9406750 A1 | 3/1994 |
| WO | WO 94/06750 * | 3/1994 |
| WO | 0146140 A1 | 6/2001 |
| WO | 0172268 A1 | 10/2001 |
| WO | 0224647 A1 | 3/2002 |
| WO | 0242268 A1 | 5/2002 |
| WO | 03047417 A1 | 6/2003 |
| WO | 2005012220 A1 | 2/2005 |
| WO | 2005116010 A1 | 12/2005 |
| WO | 2008076703 A1 | 6/2008 |
| WO | 2011147034 A1 | 12/2011 |
| WO | 2014078446 A2 | 5/2014 |
| WO | 2016199111 A1 | 12/2016 |

OTHER PUBLICATIONS

European Examination Report in corresponding European Patent Application No. 16807008.4 dated Nov. 18, 2019. 3 pages.
Indian Examination Report in corresponding Indian Patent Application No. 201847001191 dated Jan. 27, 2020. 6 pages.
Arns et al. "Design and synthesis of novel bone-targeting dual-action pro-drugs for the treatment and reversal of osteoporosis " Bioorganic & medicinal chemistry 20.6 (2012): 2131-2140.
Arns S. et al. Asymmetirc [3H]-labeling using ruthenium catalyzed transfer hydrogenation. J Label Compod Radiopharm. 2010,53(4): 205-207.
Ams et al., "Development of Dual Prodrug Conjugates for the Treatement of Osteoporosis," 93rd Canadian Chemistry Conference and Exhibition, 2010 (1 page).
Brummer O., et al. Antibody-catalzyed hydrolusis of oligomeric esters: a model for the degredation of polymeric materials. Chem Comun 2001; 19-20.

(Continued)

*Primary Examiner* — Brenda L Coleman
(74) *Attorney, Agent, or Firm* — Leason Ellis LLP

(57) ABSTRACT

The present invention relates to EP4 agonist-bisphosphonate conjugates or related compounds and uses thereof. Said conjugates or related compounds may be used to provide delivery of an EP4 agonist or related compound to a desired site of action, such as a bone. Bisphosphonate moieties, linked to the EP4 agonists via amide linkers, have been implicated in the inhibition of bone resorption and bone targeting.

19 Claims, 8 Drawing Sheets

(56) References Cited

OTHER PUBLICATIONS

Chen et al. "Determination of the rat in vivo pharmacokinetic profile of a bone-targeting dual-action pro-drug for treatment of osteoporosis." Bioconjugate chemistry 26.6 (2015): 1095-1103.
Chinese Office Action in corresponding Chinese Patent Application No. 201680038591.9 dated Jun. 6, 2019.14 pages.
Second Chinese Office Action in corresponding Chinese Patent Application No. 201680038591.9 dated Apr. 24, 2020 17 pages.
Easson et al. "Synthesis and in vitro properties of trimethylamine- and phosphonate-substituted carboranylporphyrins for application in BNCT." Bioorganic & Medicinal Chemistry 16.6 (2008): 3191-3208.
Gediya L.K. et al. Design synthesis and evaluation of novel mutual prodrugs (hybrid drugs) of all-trans-retinoic acid and histone deacetylase inhibitors with enahnced anticancer activities in breats and prostate cancer cells in vitro. J Med Chem 2008;51 (13) 3895-3904.
Hoyer S. Causes and Consequences of Distrubances of Cerebral Glucose Metabolism in Spordaic Alzheimer Disesase: Therapeutic Implications. Frontiers in Clinical Neuroscience: Neurodegeneration and Neuroprotection. Adv Exp Med Biol 2004;541: 135-152.
Huh et al. "An efficient method for one-carbon elongation of aryl aldehydes via their dibromoalkene derivatives." Tetrahedron 58.50 (2002): 9925-9932.
Extended European Search Report in corresponding European Patent Application No. 16807008.4 dated Jan. 15, 2019. 5 pages.
Second European Office Action in corresponding European Patent Application No. 16807008.4 dated May 7, 2020. 5 pages.
Liu et al. Effects of a New Anabolic Drug in Treating Postmenopausal Osteoporosis Using the Ovariectomized Rat Model,: ASBMR 2013 Annual Meeting (2013).
Liu et al. "Novel EP4 receptor agonist-bisphosphonate conjugate drug (C1) promotes bone formation and improves vertebral mechanical properties in the ovariectomized rat model of postmenopausal bone loss." Journal of Bone and Mineral Research 30.4 (2015): 670-680.
International Search Report for International Patent Application No. PCT/IB2016/053482 dated Oct. 27, 2016. 5 pages.
Lin et al. "Pharmacokinetics of alendronate: an overview." International Journal of Clinical Oractice. Supplement 101 (1999): 18-26.
Japanese Office Action in Corresponding Japanese Patent Application No. 2017-0564426 dated Jun. 15, 2020. 10 pages.
Machwate M., et al. Prostaglandin receptior EP(4) mediates the bone anabolic effects of PGE(2). Mol Pharmacol 2001;60(1): 36-41.
Roche. "Bioreversible Carriers in Drug Design: Theory and Application." Pergamon. 1987.
Velcicky et al. "Palladium-catalyzed cyanomethylation of aryl halides through domino Suzuki coupling—isoxazole fragmentation." Journal of the American Chemical Society 133.18 (2011): 6948-6951.

* cited by examiner

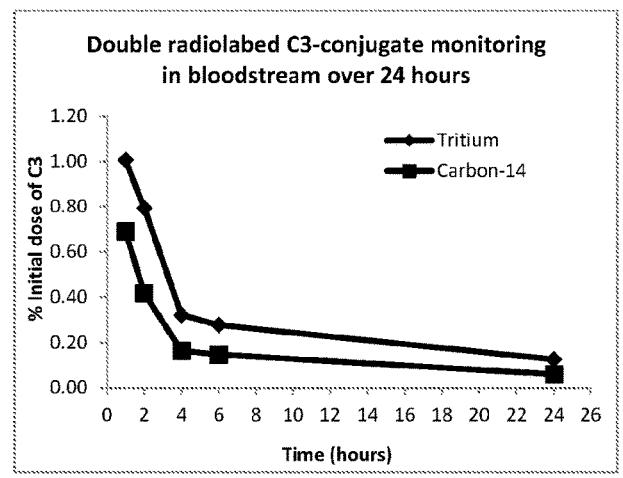 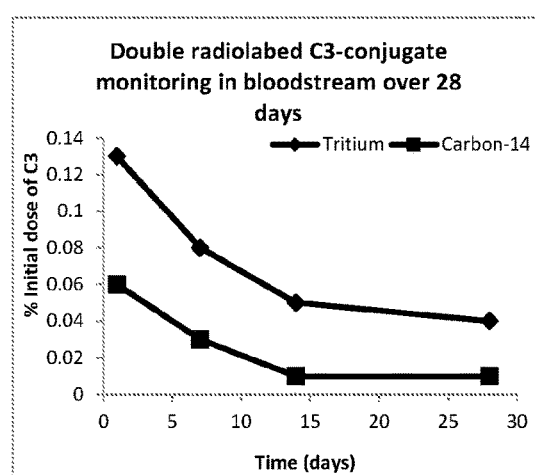
FIGURE 8A                    FIGURE 8B

AMIDE-LINKED EP4 AGONIST-BISPHOSPHONATE COMPOUNDS AND USES THEREOF

CROSS-REFERENCE TO RELATED PATENT APPLICATIONS

This application is a continuation application of U.S. patent application Ser. No. 15/735,372, filed on Dec. 11, 2017, which was a U.S. National Stage Application under 35 U.S.C. § 371 of International Patent Application No. PCT/IB2016/053482, filed Jun. 13, 2016, and claims the benefit of priority under 35 U.S.C. Section 119(e) of U.S. Application Ser. No. 62/175,118, filed Jun. 12, 2015, all of which are incorporated by reference in their entireties. The International Application was published on Dec. 15, 2016 as International Publication No. WO 2016/199111 A1.

FIELD OF INVENTION

The present invention relates to conjugate compounds and methods of making and using same.

BACKGROUND OF THE INVENTION

Prostaglandins are a sub-class of eicosanoids found in most body tissues and implicated in a variety of physiological functions in animals, including smooth muscle contraction, reproduction, autoimmunity, inflammation, reduction of intraocular pressure, etc. Prostaglandin $E_2$ ($PGE_2$) has been associated with various physiological and/or pathological conditions such as stimulation of bone formation, increase in bone mass, arthritis, pain, inflammation, cancer, multiple sclerosis, inflammatory bowel disease, etc.

$PGE_2$ binds to four receptors (EP1, EP2, EP3 and EP4). The EP4 receptor is associated with intracellular cyclic adenosine monophosphate (cAMP) production, and is distributed in a wide variety of tissue types suggesting a major role in $PGE_2$-mediated biological events, such as smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion.

A variety of EP4 agonists and related compounds have been described and include, without limitation, compounds as set forth in, for example, WO 02/24647, WO 02/42268, EP 1132086, EP 855389, EP 1114816, EP 2465506, WO 01/46140, WO 01/72268, WO 05/116010, WO 03/047417, WO2008076703, WO 2014078446 or U.S. Pat. No. 7,238,710. Many EP4 agonists have however been associated with systemic side effects.

Bisphosphonates are drugs used to strengthen bone and have been implicated in inhibiting bone resorption and bone targeting.

Prostaglandin-bisphosphonate conjugate compounds have been described in for example U.S. Pat. Nos. 5,409,911, 6,121,253 or WO 2011/147034.

SUMMARY OF THE INVENTION

The present disclosure provides, in part, conjugate compounds. The disclosure also provides synthesis methods for making the compounds, and uses of the compounds.

In one aspect, the present disclosure provides a compound according to Formula I, or a pharmaceutically acceptable salt thereof:

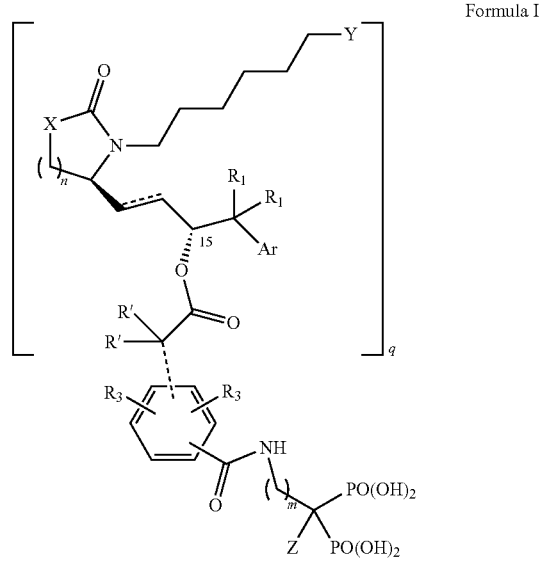

Formula I where:
X may be —$CH_2$—, —S—, —O—, or —NH—;
Y may be COOR', optionally substituted tetrazole, or C(O)NHSO$_2$R;
Z may be OH or H;
R may be optionally substituted lower alkyl or optionally substituted aryl;
n may be 1, 2, or 3;
m may be 0, 1, 2, 3, 4, 5, or 6;
q may be 1, or 2;
$R_1$ may be independently H or halogen;
Ar may be aryl, substituted aryl, or heteroaryl;
$R_3$ may be each independently H, OR', halogen, CN, or C(O)R';
R' may be each independently H or lower alkyl, or two R's may form a ring of up to 6 carbons; and
--- may be a double or single bond.

In some embodiments, the compound may be: sodium (4-(4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxybutane-1,1-diyl)bis(hydrogen phosphonate); sodium (3-(4-(2-MR,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxypropane-1,1-diyl)bis(hydrogen phosphonate); or sodium (6-(4-(2-MR,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxyhexane-1,1-diyl)bis(hydrogen phosphonate).

In alternative aspects, the present disclosure provides a compound or a pharmaceutically acceptable salt thereof, the compound including at least one EP4 agonist or related moiety linked to an amide linker through an ester bond and an amino bisphosphonate moiety linked to the amide linker through an amide bond. The amide linker may include up to three carboxylic acid groups and the hydroxyl groups of two EP4 agonists or related moieties may be linked to two carboxylic acid groups of the amide linker, to form the ester bonds, and the other carboxylic acid of the amide linker group may be linked to the amino group of the bisphosphonate to form the amide bond.

In alternative aspects, the present disclosure provides a compound or a pharmaceutically acceptable salt thereof, the compound including at least one EP4 agonist or related moiety linked to an amide linker through an ester bond at position C-15, or equivalent, and an amino bisphosphonate moiety linked to the amide linker through an amide bond.

In some embodiments, the compound may be hydrolyzable in vivo. In some embodiments, the compound may be inactive prior to hydrolyzation. In some embodiments, the amide bond of the compound may be resistant to hydrolysis in vivo.

The amide linker may be 4-(carboxymethyl) benzoic acid or 3,5-bis-(carboxymethyl)benzoic acid.

In alternative aspects, the present disclosure provides a composition including a compound according to the invention in combination with a carrier.

In alternative aspects, the present disclosure provides a pharmaceutical composition including a compound according to the invention, in combination with a pharmaceutically acceptable carrier.

In alternative aspects, the present disclosure provides methods of selectively delivering a compound to bone or an associated site, by administering an effective amount of a compound or composition according to the invention to a subject in need thereof.

In alternative embodiments, the associated site may be a site adjacent to a bone in need of treatment. In alternative embodiments, the bone in need of treatment may be a green stick fracture, compound fracture, lateral fracture, pathologic fracture resulting from an invasive tumor, compression fracture, or a fracture requiring a surgical procedure for realignment of a bone.

In alternative aspects, the present disclosure provides a method of selectively delivering a conjugate compound to bone or an associated site, by administering an effective amount of a compound according to the invention or a pharmaceutically acceptable salt thereof to a subject in need thereof.

In alternative aspects, the present disclosure provides a method of treating or preventing a condition associated with abnormal or excessive bone loss, or with abnormal or reduced bone resorption, or with abnormal calcium metabolism, or that would be benefited by administration of an EP4 agonist or related compound, by administering an effective amount of a conjugate compound according to the invention or a pharmaceutically acceptable salt thereof to a subject in need thereof.

In some embodiments, the compound may bind to bone. In some embodiments, the compound may be hydrolyzed after binding to bone. In some embodiments, the compound may be inactive prior to hydrolyzation. In some embodiments, the compound may release an active agent, such as an EP4 agonist or related compound, after hydrolyzation. In some embodiments, the amide bond of the compound may be resistant to hydrolysis in vivo. In some embodiments, the bisphosphonate moiety of the compound may remain attached to the bone.

In alternative aspects, the present disclosure provides for use of an effective amount of a conjugate compound according to the invention or a pharmaceutically acceptable salt thereof for treating or preventing a condition associated with abnormal or excessive bone loss, or with abnormal or reduced bone resorption, or with abnormal calcium metabolism, or that would be benefited by administration of an EP4 agonist or related compound, in a subject.

In alternative embodiments, the condition may be osteoporosis, Paget's disease, abnormally increased bone turnover, bone graft, periodontal disease, alveolar bone loss, tooth loss, bone fracture, periprostheticosteolysis, osteogenesis imperfecta, metastatic bone disease, or irritable bowel syndrome.

In alternative embodiments, the subject may be a human.

In alternative aspects, the present disclosure provides a method of preparing a conjugate compound, by providing at least one EP4 agonist or related moiety comprising a hydroxyl group, an amide linker comprising at least two carboxylic acid groups, and a bisphosphonate moiety comprising an amino group; reacting one of the carboxylic acid groups of the amide linker with the hydroxyl group of the EP4 agonist or related moiety, to form an ester bond, and reacting the other carboxylic acid of the amide linker group with the amino group of the bisphosphonate to form an amide bond. In some embodiments, the amide linker may include up to three carboxylic acid groups and the hydroxyl groups of two EP4 agonists or related moieties may be reacted with two carboxylic acid groups of the amide linker, to form the ester bonds, and the other carboxylic acid of the amide linker group may be reacted with the amino group of the bisphosphonate to form an amide bond.

This summary does not necessarily describe all features of the invention.

BRIEF DESCRIPTION OF THE DRAWINGS

These and other features will become more apparent from the following description in which reference is made to the appended drawings wherein:

FIG. 8A is a graph showing the release of double labelled C3-conjugate into rat bloodstream over 24 hours;

FIG. 8B is a graph showing the release of double labelled C3-conjugate into rat bloodstream over 28 days;

DETAILED DESCRIPTION

Figure 1:
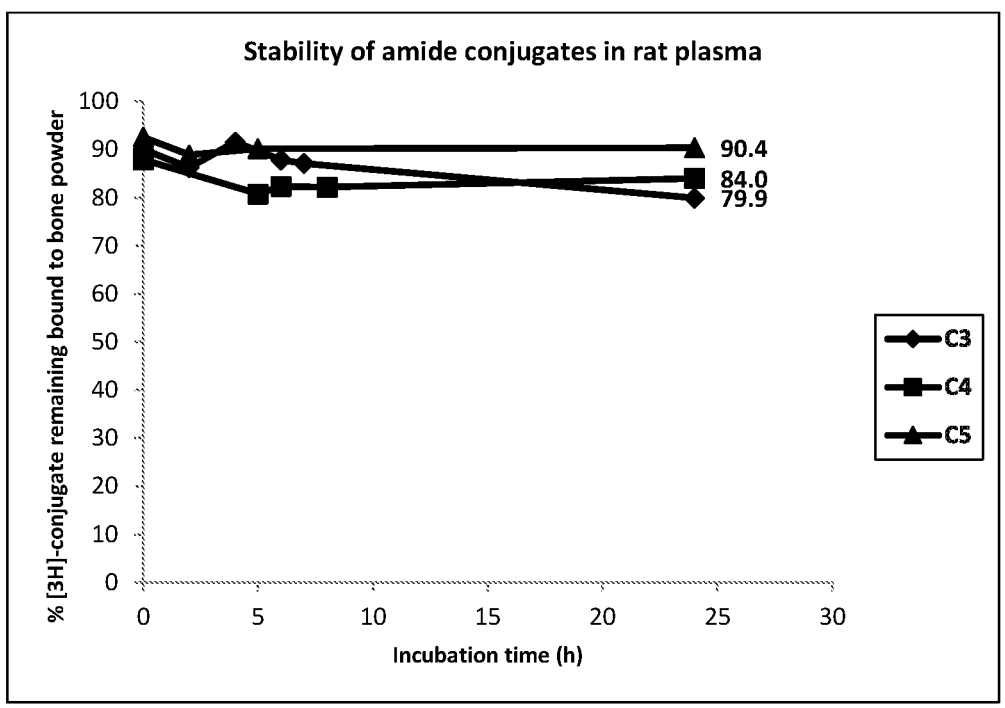
FIG. 1 is a graph showing the stability of tritium-labelled C3-, C4- and C5-conjugate compounds in rat plasma.

The present disclosure provides, in part, EP4 agonist-bisphosphonate conjugates or related compounds and uses thereof. In some embodiments, the EP4 agonist-bisphosphonate conjugates or related compounds may provide delivery of an EP4 agonist or related compound to a site of action, such as bone.

By "EP4 agonist-bisphosphonate conjugate compound" or "conjugate compound" or simply "conjugate," as used herein, is meant a compound including an EP4 agonist or related compound linked to a bisphosphonate through an amide linker. Accordingly, by "conjugated" is meant the linkage of a bisphosphonate and another compound, such as an EP4 agonist or related compound, via an amide linker as described herein or known in the art. Without being bound to any particular theory, the amide linkage may be resistant to hydrolysis in vivo and may thus provide a higher chemical stability to the conjugate compound. It is to be understood that more than one EP4 agonists or related compounds may be conjugated to the amide linker. In some embodiments, more than one EP4 agonists or related compounds may be conjugated to the amide linker, which may be conjugated to a single bisphosphonate.

EP4 agonists and related compounds are described in, for example, WO 02/24647, WO 02/42268, EP 1132086, EP 855389, EP 1114816, EP 2465506, WO 01/46140, WO 01/72268, WO 05/116010, WO 03/047417, WO2008076703, WO 2014078446, U.S. Pat. No. 7,238,710 etc. and include, without limitation, compounds containing at least one hydroxyl group, as described herein or known in the art, capable of forming an ester linkage with another compound. In some embodiments, EP4 agonists having a hydroxyl group at position "C-15" (nomenclature based on the corresponding numbering of prostaglandin $E_2$), may be used to prepare conjugate compounds as described herein. In some embodiments, EP4 agonists include related compounds (for example, an ONO agonist or other compounds described herein or known in the art) that have a hydroxyl group at a position equivalent to C-15 of prostaglandin $E_2$ and that may be used to prepare conjugate compounds as described herein.

An "EP4 agonist" moiety, as described herein, is the portion of an EP4 agonist or related compound (a "related moiety") that is conjugated via a hydroxyl group, such as the C-15 or equivalent hydroxyl group, to another compound, such as an amide linker, to form an ester bond, in the context of a conjugate compound.

In some embodiments, an EP4 agonist may have the following general structure:

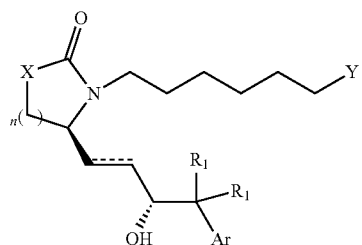

where X may be —$CH_2$—, —S—, —O—, or —NH—; Y may be COOR', optionally substituted tetrazole, or C(O)$NHSO_2$R; R may be optionally substituted lower alkyl or optionally substituted aryl; n may be 1, 2, or 3; $R_1$ may be independently H or halogen; Ar may be aryl, substituted aryl, or heteroaryl; R' may be H or lower alkyl; and ⁓ may be a double or single bond.

In some embodiments, an EP4 agonist related compound may be optionally substituted in the alkyl chain. In some embodiments, the alkyl chain of an EP4 agonist related compound may be saturated or unsaturated. In some embodiments, an EP4 agonist related compound may have a heteroatom (such as sulfur) in the alkyl chain, as found for example in an ONO agonist.

In some embodiments, an EP4 agonist related compound may include, without limitation:

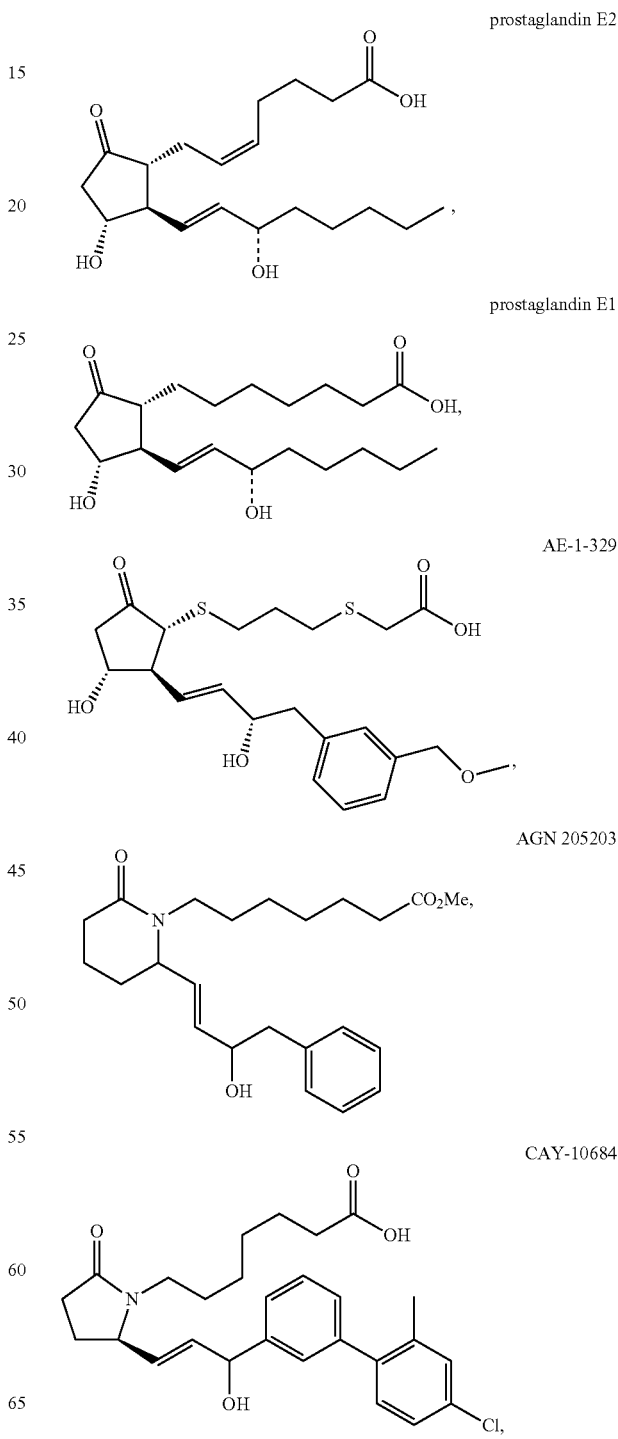

KAG-308

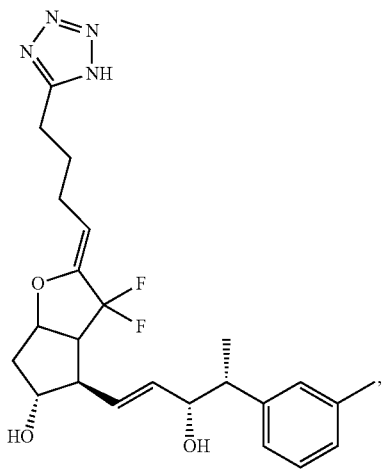

KMN-80

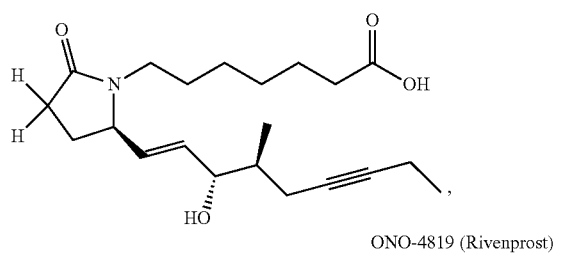

ONO-4819 (Rivenprost)

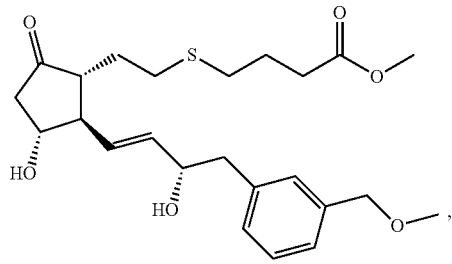

Compound A

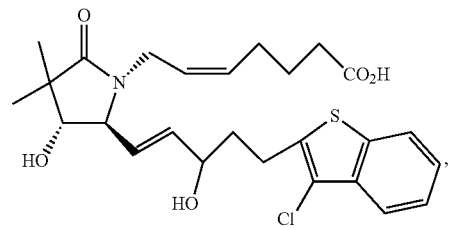

Compound B

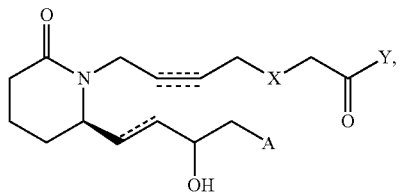

where a dashed line indicates the presence or absence of a bond, A is optionally substituted phenyl, X is CH2, 0 or S, Y is $OR^1$ or $N\ R^1R^2$ and $R^1$ and $R^2$ are independently H or C1-6 alkyl, CP-536,745-01, CP-043,305-02, CP-044,519-02 or ONO-4232.

By "bisphosphonate" as used herein is meant an amino-bisphosphonate compound. Any known bisphosphonate which has a secondary or primary amine functionality capable of coupling to an EP4 agonist or related compound or other compound, such as a linker, and which targets in vivo to bone may be used, whether or not that particular bisphosphonate has bone resorption inhibiting activity. In some embodiments, a suitable bisphosphonate may exhibit poor or no bone resorption inhibiting activity.

In some embodiments, bisphosphonates may have the following general structure, where m may be 1, 2, 3, 4, 5 or 6.

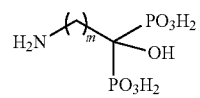

A "bisphosphonate moiety," as used herein, is the portion of a bisphosphonate that is conjugated via the amino group to another compound, such as an amide linker, to form an amide bond, in the context of a conjugate compound, as described herein.

Bisphosphonates include, without limitation, alendronic acid, 4-amino-1-hydroxybutylidene-1, 1-bisphosphonic acid; alendronate (also known as alendronate sodium or alendronate monosodium trihydrate), 4-amino-1-hydroxybutylidene-1, 1-bisphosphonic acid monosodium trihydrate; alendronic acid and alendronate are described in U. S. Pat. No. 4,922,007, to Kieczykowski et al., issued May 1,1990; U.S. Pat. No. 5,019,651, to Kieczykowski et al., issued May 28,1991; U.S. Pat. No. 5,510,517, to Dauer et al., issued Apr. 23,1996; U.S. Pat. No. 5,648,491, to Dauer et al., issued Jul. 15,1997; 6-amino-1-hydroxyhexylidene-1,1-bisphosphonic acid (neridronate); 3-amino-1-hydroxypropylidene-1,1-bisphosphonic acid (pamidronate); or pharmaceutically acceptable salts thereof, or mixtures thereof.

Examples of EP4 agonists include compounds A and B and examples of clinically active bisphosphonates (BPs) include alendronate/alendronic acid (C), pamidronate (D) or neridronate (E).

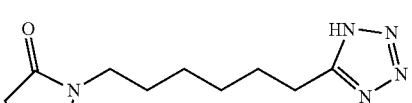

A

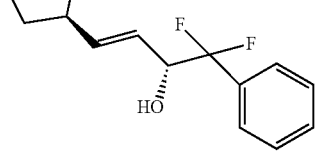

B

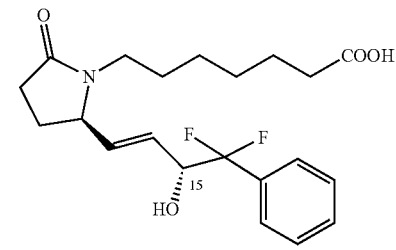

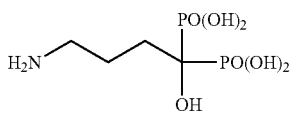

C

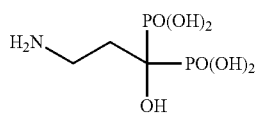

D

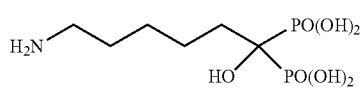

E

By an "amide linker," as used herein, is meant a molecule, as described herein or known in the art, which may be used to link a hydroxyl group, such as the C-15 or equivalent hydroxyl group, of an EP4 agonist or related compound with the amino group of a bisphosphonate. In some embodiments, a suitable amide linker may be capable of being conjugated, via an ester unit, with a hydroxyl group, such as the C-15 or equivalent hydroxyl group, of an EP4 agonist or related compound. In some embodiments, a suitable amide linker may be capable of being conjugated with the amino group of a bisphosphonate to form an amide bond. In some embodiments, a suitable amide linker may be capable of being conjugated, via an ester unit, with a hydroxyl group, such as the C-15 or equivalent hydroxyl group, of an EP4 agonist or related compound, and also with the amino group of a bisphosphonate to form an amide bond (i.e., a bifunctional linker). In some embodiments, a suitable amide linker may be capable of being conjugated, via an ester unit, with the hydroxyl groups, such as the C-15 or equivalent hydroxyl groups, of multiple EP4 agonists or related compounds, and also with the amino group of a single bisphosphonate.

In some embodiments, a suitable amide linker may contain a carboxylic acid group capable of reacting with a hydroxyl group, such as the C-15 or equivalent hydroxyl group, of an EP4 agonist or related compound to form an ester linkage. In some embodiments, a suitable amide linker may contain a carboxylic acid group capable of reacting with the amino group of a bisphosphonate. In some embodiments, a suitable amide linker may contain carboxylic acid groups capable of reacting with a hydroxyl group, such as the C-15 or equivalent hydroxyl group, of an EP4 agonist or related compound, to form an ester linkage, and with the amino group of a bisphosphonate to form an amide bond. In some embodiments, a suitable amide linker may be a bifunctional dicarboxylic acid chain up to about 12 carbons in length, optionally including an aryl and/or heteroatoms (for example, O, S, or N), where one of the carboxylic acid groups may be capable of reacting with a hydroxyl group, such as the C-15 or equivalent hydroxyl group, of an EP4 agonist or related compound, to form an ester linkage, and the other carboxylic acid group may be capable of reacting with the amino group of a bisphosphonate to form an amide bond.

In some embodiments, a suitable amide linker may have the following general structure:

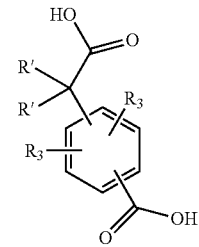

where $R_3$ may each independently be H, OR', halogen, CN, or C(O)R'; and R' may each independently be H or lower alkyl, or two R's may form a ring of up to 6 carbons; where one of the carboxylic acid groups may be capable of reacting with a hydroxyl group, such as the C-15 or equivalent hydroxyl group, of an EP4 agonist or related compound, to form an ester linkage, and the other carboxylic acid group (e.g., the benzoic acid moiety) may be capable of reacting with the amino group of a bisphosphonate to form an amide bond.

In some embodiments, a suitable amide linker may have the following general structure:

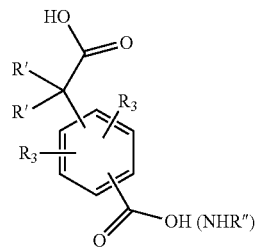

where $R_3$ may each independently be H, OR', halogen, CN, or C(O)R'; and R' may each independently be H or lower alkyl, or two R's may form a ring of up to 6 carbons; where the carboxylic acid group may be capable of reacting with a hydroxyl group, such as the C-15 or equivalent hydroxyl group, of an EP4 agonist or related compound, to form an ester linkage, and the other carboxylic acid group (e.g., the benzoic acid moiety) may be capable of reacting with the amino group of a bisphosphonate (NHR") to form an amide bond.

In some embodiments, a suitable amide linker may have the following general structure:

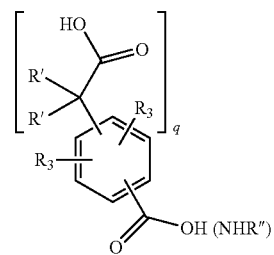

where q may be 1 or 2, $R_3$ may each independently be H, OR', halogen, CN, or C(O)R'; and R' may each independently be H or lower alkyl, or two R's may form a ring of up to 6 carbons; where one or more of the carboxylic acid groups may be capable of reacting with a hydroxyl group, such as the C-15 or equivalent hydroxyl group, of an EP4 agonist or related compound, to form an ester linkage, and the remaining carboxylic acid group (e.g., the benzoic acid moiety) may be capable of reacting with the amino group of a bisphosphonate (NHR") to form an amide bond.

In some embodiments, a suitable amide linker may have the following general structure:

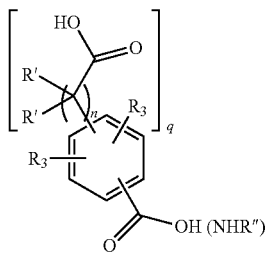

where n may be 1, 2 or 3; q may be 1 or 2; R3 may each independently be H, OR', halogen, CN, or C(O)R'; and R' may each independently be H or lower alkyl, or two R's may form a ring of up to 6 carbons; where one or more of the carboxylic acid groups may be capable of reacting with a hydroxyl group, such as the C-15 or equivalent hydroxyl group, of an EP4 agonist or related compound, to form an ester linkage, and the remaining carboxylic acid group (e.g., the benzoic acid moiety) may be capable of reacting with the amino group of a bisphosphonate (NHR") to form an amide bond.

In some embodiments, a suitable amide linker may include, without limitation, 4-(carboxymethyl) benzoic acid or 3,5-bis-(carboxymethyl)benzoic acid.

In some embodiments, conjugate compounds according to the present disclosure include a compound according to Formula I, or a pharmaceutically acceptable salt thereof:

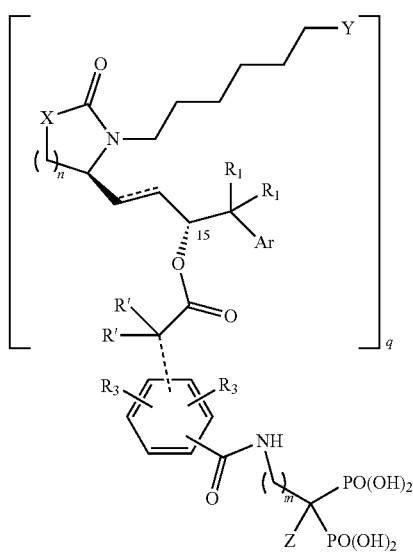

Formula I wherein:
X may be —$CH_2$—, —S—, —O—, or —NH—;
Y may be COOR', optionally substituted tetrazole, or C(O)NHSO$_2$R;
Z may be OH or H;
R may be optionally substituted lower alkyl or optionally substituted aryl;
n may be 1, 2, or 3;
m may be 0, 1, 2, 3, 4, 5, or 6;
q may be 1, or 2;
$R_1$ may be independently H or halogen;
Ar may be aryl, substituted aryl, or heteroaryl;
$R_3$ may be each independently H, OR', halogen, CN, or C(O)R';
R' may be each independently H or lower alkyl, or two R's may form a ring of up to 6 carbons; and
--- may be a double or single bond. It is to be noted that the C-15 position is indicated in Formula I.

"Alkyl" as used herein refers to a straight or branched hydrocarbon chain group consisting solely of carbon and hydrogen atoms, containing no unsaturation and including, for example, from one to ten carbon atoms ("lower alkyl"), and which is attached to the rest of the molecule by a single bond. Unless stated otherwise specifically in the specification, the alkyl group may be optionally substituted by one or more substituents as described herein. Unless stated otherwise specifically herein, it is understood that the substitution can occur on any carbon of the alkyl group. Examples of straight or branched chain alkyl groups include, but are not limited to, methyl, trifluoromethyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, 1-heptyl, or 1-octyl.

By a "ring structure" is meant a cycloalkyl, aryl, heteroaryl, or any cyclic structure that may be optionally substituted.

"Aryl" as used herein refers to a monocylic or bicycled ring structure wherein all rings are aromatic and are formed of carbon atoms, for example, phenyl or naphthyl groups. Unless stated otherwise specifically herein, the term "aryl" is meant to include aryl groups optionally substituted by one or more substituents as described herein. Accordingly, in some embodiments, the term "aryl" may refer to heteroaryl with, for example, rings of 5 or 6 or more atoms containing one or two heteroatoms such as N, S, or O.

"Halo" refers to halogen groups such as bromo, chloro, fluoro, iodo, etc. In some embodiments, suitable halogens include fluorine.

Any group described herein, such as alkyl, aryl, tetrazole, etc., may be substituted or unsubstituted. When substituted, a group may be substituted with any desired substituent or substituents such as one or more of the following group: H, alkyl ($C_{1-10}$), alkenyl ($C_{2-10}$), alkynyl ($C_{2-10}$), aryl (5-12 members), arylalkyl, arylalkenyl, or arylalkynyl, each of which may optionally contain one or more heteroatoms selected from O, S, P, N, F, Cl, Br, I, or B, and each of which may be further substituted, for example, by =O; or optionally substituted forms of acyl, arylacyl, alkyl-alkenyl-, alkynyl- or arylsulfonyl and forms thereof which contain heteroatoms in the alkyl, alkenyl, alkynyl or aryl moieties; halogen (e.g., chloro, iodo, bromo, or fluoro); hydroxyl; $C_{1-10}$ alkoxyl; amino (primary, secondary, or tertiary); nitro; thiol; thioether; imine; cyano; amido; carbamoyl; phosphonato; bisphosphonate; phosphine; carboxyl; thiocarbonyl; sulfonyl; sulfonamide; ketone; aldehyde; ester; oxo; haloalkyl (e.g., trifluoromethyl); cycloalkyl, which may be monocyclic or fused or non-fused polycyclic (e.g., cyclopropyl, cyclobutyl, cyclopentyl, or cyclohexyl), or non-aromatic heterocyclic, which may be monocyclic or fused or non-fused polycyclic (e.g., pyrrolidinyl, piperidinyl, piperazinyl, morpholinyl, or thiazinyl); and aromatic carbocyclic or heterocyclic, monocyclic or fused or non-fused polycyclic (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl). Specific substituent groups include benzyloxy; O-alkyl; O-aryl; aryl; aryl-lower alkyl, etc. A substituted group may have 1, 2, 3, 4, 5, 6, 7, 8, 9 or 10 substituent groups. In some embodiments, these substituent groups may optionally be further substituted with a substituent as listed herein. Substituents may also be optionally substituted by a bridge structure, for example —OC(O)O— or —OC(O)NH—. In some embodiments, substituents are not further substituted.

"Optional" or "optionally" means that the subsequently described event of circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution. Examples of optionally substituted alkyl groups include, without limitation, methyl, ethyl, propyl, etc. Similarly, "optionally substituted tetrazole" means that the tetrazole group may or may not be substituted and the description includes both substituted tetrazoles and tetrazoles having no substitution.

Compounds may be in acid, base, or salt form.

Throughout this application, it is contemplated that the term "compound" or "compounds" refers to the compounds and conjugates discussed herein and includes precursors, intermediates, and derivatives of the compounds, including acyl-protected derivatives, and pharmaceutically acceptable salts of the compounds, precursors, and derivatives. The invention also includes prodrugs of the compounds, pharmaceutical compositions including the compounds and a pharmaceutically acceptable carrier, and pharmaceutical compositions including prodrugs of the compounds and a pharmaceutically acceptable carrier.

In some embodiments, all of the compounds of the invention contain at least one chiral center. In some embodiments, the compounds of the invention can have one or more chiral centers and/or double bonds. In some embodiments, the formulations, preparation, and compositions including compounds according to the invention can include mixtures of stereoisomers, individual stereoisomers, and enantiomeric mixtures, mixtures of multiple stereoisomers, double-bond isomers (i.e., geometric E/Z isomers) or diastereomers (e.g., enantiomers (i.e., (+) or (−)) or cis/trans isomers). In some embodiments, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. In general, the compound may be supplied in any desired degree of chiral purity.

Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

In some embodiments, the EP4 agonist or other agent-bisphosphonate conjugate compounds may be delivered directly to bone.

In some embodiments, an EP4 agonist-bisphosphonate conjugate compound or related compound, as described herein, may exhibit efficient uptake to bone. By "efficient uptake" as used herein is meant the amount of conjugate compound bound to bone as a percentage of the initial dosage. In alternative embodiments, by "efficient uptake" as used herein is meant the uptake of at least about 5% of an EP4 agonist-bisphosphonate conjugate compound as described herein, compared to the initial dosage. In alternative embodiments, at least about 5%, 6%, 7%, 8%, 9%, 10%, 11%, 12%, 13%, 14%, 15%, 16%, 17%, 18%, 19%, 20%, 21%, 22%, 23%, 24%, 25%, or more, an EP4 agonist-bisphosphonate conjugate compound as described herein, may be bound to bone in a suitable period of time, such as 5 to 24 hours, after the initial dosage but prior to the initiation of hydrolysis of the conjugate compound.

The conjugate compounds may be hydrolyzable in vivo to release the EP4 agonist or other compound conjugated to the bisphosphonate. In some embodiments, the EP4 agonist-bisphosphonate conjugate compounds may be hydrolyzable in vivo to release one or more EP4 agonists or related compounds only (with a free alcohol, such as the C-15 or equivalent position,), and not the bisphosphonate, which may remain conjugated to the amide linker via the amide bond. Without being bound to any particular theory, the amide linkage may result in increased stability of the conjugate compounds. In some embodiments, once attached to bone, the conjugate compounds may not be capable of releasing detectable or substantial amounts of active bisphosphonate. For example, conjugates 1 (alendronate conjugate), 2 (pamidronate conjugate), or 3 (neridronate conjugate), which contain an EP4 agonist linked through the C-15 hydroxyl via an ester linker to the bisphosphonate moiety, may be hydrolyzed in vivo to release the EP4 agonist and result in the formation of fragments 4, 5, or 6, which contain the linker attached to the bisphosphonate moiety via an amide group.

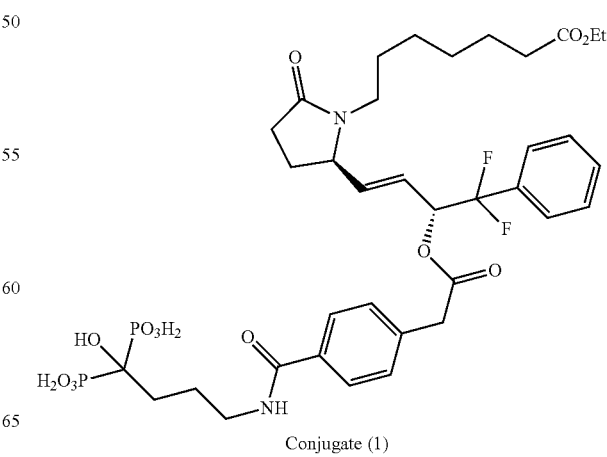

Conjugate (1)

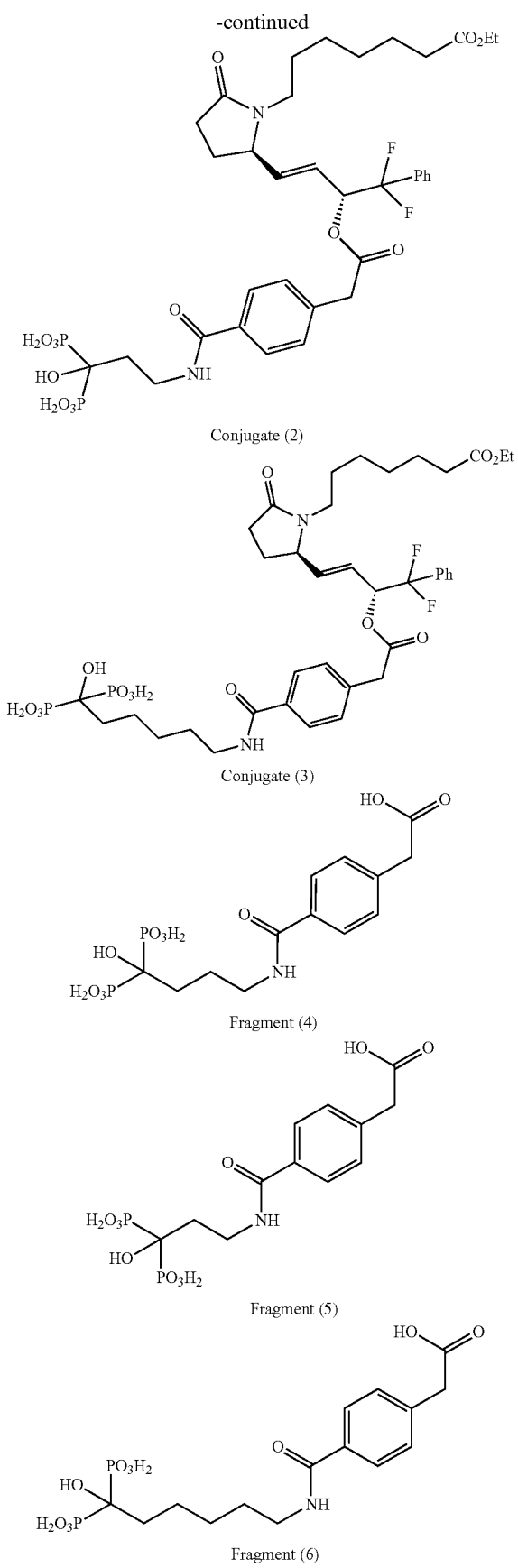

Conjugate (2)

Conjugate (3)

Fragment (4)

Fragment (5)

Fragment (6)

In some embodiments, the fragment (e.g., 4, 5 or 6) that may remain attached to bone after liberation of the EP4 agonist, namely, 2-(4-((4-hydroxy-4,4-diphosphonobutyl)carbamoyl)phenyl)acetic acid, in the case of the alendronate analog, may have little or no biological activity as an inhibitor of bone resorption.

In alternative embodiments, the conjugate compounds may be inactive until hydrolyzed and the agents conjugated to the bisphosphonates are released. For example, EP4 agonist-bisphosphonate conjugate compounds may be inactive until hydrolyzed, releasing only the EP4 agonist or related compound moieties. In some embodiments, the linkage of the EP4 agonists or related compounds through the C-15 hydroxyl via an ester bond may allow slow release of the EP4 agonists or related compouns. The EP4 agonist moieties or related compounds, containing a free alcohol at for example C-15, may be active. In some embodiments, the conjugate compounds may be inactive until attached to bone, after which they may be hydrolyzed and the agents conjugated to the bisphosphonate moiety and amide linker released. For example, EP4 agonist-bisphosphonate conjugate compounds may be inactive until attached to bone, after which they may be hydrolyzed and the EP4 agonist moieties or related compounds conjugated to the bisphosphonate moiety and amide linker released.

In some embodiments, the bisphosphonate moiety may remain attached to the bone and may be biologically inactive (e.g., have little to no detectable bone resorption activity). By "release" as used herein is meant the liberation of the agent(s) conjugated to the bisphosphonate such as by hydrolysis or enzyme action, from a conjugate compound. In alternative embodiments, by "release" as used herein is meant the liberation of one or more EP4 agonist moieties or related compounds, for example, by hydrolysis or enzyme action, from an EP4 agonist-bisphosphonate conjugate compound as described herein. In alternative embodiments, at least about 5% to about 100%, for example, about 5%, 6%, 7%, 8%, 9% 10%, 11%, 12%, 13%, 14%,15%, 20%, 25%, 30%, 35%, 40%, 45%, 50%, 55%, 60%, 65%, 70%, 75%, 80%, 85%, 90%, 95%, or 100% or any value there between, of the EP4 agonists or related compounds may be released from an EP4 agonist-bisphosphonate conjugate compound, as described herein, in a suitable period of time. The release may be measured, for example, in blood or plasma, after the conjugate has become bound to bone in vivo, or in any suitable system or assay described herein or known in the art. The release may also be measured by loss of radiolabel associated with the EP4 agonist or related compound from the bone after various time periods when compared to earlier time periods. In alternative embodiments, the release may take a period of time, for example, about 1 day to about 30 days, or any value or set of values between this range, for example, about 7 days to about 14 days, such as about 7, 8, 9, 10, 11, 12, 13, or 14 days. In some embodiments, the release may differ from in plasma and from bone. Accordingly, in some embodiments, a conjugate compound that is stable or exhibits slow release in plasma may be useful in that it may allow for binding to bone prior to release of the EP4 moieties or related compounds. In alternative embodiments, the ability of the conjugate compound to be targeted to bone and to release the EP4 moieties or related compounds from bone may be the determinative characteristic.

In alternative embodiments, the fragment remaining after hydrolysis and liberation of the EP4 agonist (such as fragments 4, 5, or 6 or any fragment including a bisphonate moiety and optionally an amide linker) may have have little or no biological activity. For example, the fragment remaining after hydrolysis and liberation of the EP4 agonist or related compound from a conjugate compound that is delivered to bone may have little or no biological activity as an inhibitor of bone resorption. In some embodiments, and without being bound to any particular theory, a conjugate compound that is delivered to bone may enhance bone formation, but have little to no effect on bone resorption intact to, for example, allow natural bone remodeling with a net gain in bone.

EP4 agonist-bisphosphonate conjugates or related compounds may be prepared as described herein or elsewhere. It is to be understood that modifications of the methods and schemes as described herein, when performed using standard techniques or achieved by routine experimentation, are encompassed herein.

In some embodiments, suitable conjugates may be prepared, for example, by linking the hydroxyl moiety of a compound (e.g., EP4 agonists or related compounds) using bisphosphonate with a free primary or secondary amino moiety, via an amide linker, using the techniques described herein or modifications thereof, as known in the art.

Therapeutic Indications

A variety of conditions or disorders in humans and other mammals involve or are associated with abnormal or excessive bone loss, or with abnormal or reduced bone resorption, or with abnormal calcium metabolism. Such conditions or disorders include, but are not limited to, osteoporosis, which may include low bone mass and microarchitectural deterioration of bone tissue, with a consequent increase in bone fragility and susceptibility to fracture, glucocorticoid-induced osteoporosis, Paget's disease, abnormally increased bone turnover, bone graft, periodontal disease, alveolar bone loss, tooth loss, bone fractures, periprostheticosteolysis, osteogenesis imperfecta, metastatic bone disease, etc. In addition, a variety of conditions or disorders in humans and other mammals may be benefited from the administration of an EP4 agonist or related compound, such as irritable bowel syndrome (IBD), arthritis, pain, cancer, multiple sclerosis, smooth muscle relaxation, intraocular pressure, pain (such as inflammatory, neuropathic and visceral pain), inflammation, neuroprotection, lymphocyte differentiation, allergic activities, promotion of sleep, renal regulation, gastric or enteric mucus secretion duodenal bicarbonate secretion, etc.

Accordingly, the conjugate compounds, as described herein, may be used to treat or prevent conditions or disorders associated with abnormal or excessive bone loss, or with abnormal or reduced bone resorption, or with abnormal calcium metabolism, or may be used to treat any condition or disorder that would benefit from targeting a therapeutic agent to the bone or by administration of EP4 agonists or related compounds. In some embodiments, conjugate compounds including multiple EP4 agonist moieties or related compounds may be particularly useful.

In alternative embodiments, the invention provides methods of enhancing or elevating levels of bone stimulation in animal subjects, such as, veterinary and human subjects. This elevation can be useful for the prevention or treatment of conditions or disorders associated with abnormal or excessive bone loss, or with abnormal or reduced bone resorption, or with abnormal calcium metabolism.

The effectiveness of the conjugates in prevention or treatment of conditions or disorders associated with abnormal or excessive bone loss, or with abnormal or reduced bone resorption, or with abnormal calcium metabolism, or that may benefit from targeting a therapeutic agent to the bone or by administration of an EP4 agonist or related compound, may be confirmed by testing the ability of the conjugates to enhance or elevate bone stimulation, or by measuring targetting of the conjugates to, or retention in, various organs or tissues, using standard techniques.

For example, the conjugates may be evaluated first for in vitro for stability in plasma and then in normal animals (e.g., rats) for selective uptake into bones or other organs or tissue, and slow release of the therapeutic molecules, such as free EP4 agonists or related compounds. When suitable conjugate(s) are identified, optimized compound(s) may be evaluated in animal models of osteoporosis or for example in an in vitro model of osteogenesis, i.e., neonatal rat calvaria cell cultures. Then the compounds may be used in for example in vivo or other assays to show efficacy and tolerability suitable for further development as novel therapies for treatment of disorders and conditions as described herein or found in the art.

In general, the methods of the invention are effected by administering a conjugate compound according to the present disclosure to a subject in need thereof, or by contacting a cell or a sample with a compound according to the present disclosure, for example, a pharmaceutical composition comprising a therapeutically effective amount of the compound.

Pharmaceutical & Veterinary Compositions, Dosages, and Administration

Pharmaceutical compositions including the conjugate compounds according to the present disclosure, or for use according to the present disclosure, are contemplated as being within the scope of the invention. In some embodiments, pharmaceutical compositions including an effective amount of a conjugate compound as described herein are provided.

In some embodiments, the conjugate compounds according to the present disclosure target bone or a site at which bone growth stimulation is required. Such a site includes both the area in the immediate vicinity to a section of bone or group of bones in need of treatment in a subject in need thereof or a region inside the bone, including the site of a fracture or opening which occurs naturally or is intentionally made in the bone or group of bones. Bones in need of treatment may include green stick fractures, compound fractures, lateral fractures, pathologic fractures resulting from invasive tumors, compression fractures and fractures that require surgical procedures for realignment of bones.

The conjugate compounds and their pharmaceutically acceptable salts, stereoisomers, solvates, and derivatives may be useful because they have pharmacological activity in animals, including humans. In some embodiments, the conjugate compounds according to the present disclosure may be stable in plasma, when administered to a subject. In alternative embodiments, the EP4 agonist or other agent-bisphosphonate conjugate compounds may be administered at lower doses compared to each of the individual components. In some embodiments, the EP4 agonist or other agent-bisphosphonate conjugate compounds may reduce the systemic side effects associated with EP4 agonists.

In some embodiments, conjugate compounds according to the present disclosure, or for use according to the present disclosure, may be provided in combination with any other active agents or pharmaceutical compositions where such combined therapy is useful to treat or prevent conditions or disorders associated with abnormal or excessive bone loss, or with abnormal or reduced bone resorption, or with abnormal calcium metabolism, for example, to treat any condition or disorder described herein or that would benefit from targeting a therapeutic agent to the bone or by the administration of an EP4 agonist or related compound.

In some embodiments, conjugate compounds according to the invention, or for use according to the present disclosure, may be provided in combination with one or more agents useful in the prevention or treatment of conditions or disorders associated with abnormal or excessive bone loss, or with abnormal, or with abnormal calcium metabolism to treat any condition or disorder described herein or that would benefit from targeting a therapeutic agent to the bone.

Combinations of conjugate compounds according to the present disclosure, or for use according to the present disclosure, and other therapies useful in the prevention or treatment of conditions or disorders associated with abnormal or excessive bone loss, abnormal calcium metabolism, cancer, or any disorder associated with bone or that would benefit from targeting a therapeutic agent to the bone, may be administered separately or in conjunction. The administration of one agent or conjugate compound may be prior to, concurrent to, or subsequent to the administration of other agent(s) or conjugate compounds.

In alternative embodiments, while the conjugate compounds according to the invention may themselves be considered "prodrugs," the conjugate compounds may be supplied as further prodrug or protected forms, which release the compound after administration to a subject. For example, the compound may carry a protective group which is split off by hydrolysis in body fluids, e.g., in the bloodstream, thus releasing the active compound or is oxidized or reduced in body fluids to release the compound. Accordingly, a "prodrug" is meant to indicate a compound that may be converted under physiological conditions (e.g., enzymatically) or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a subject.

The term "prodrug" is also meant to include any covalently bonded carriers which release the active compound of the invention in vivo when such prodrug is administered to a subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and acetamide, formamide, and benzamide derivatives of amine functional groups in the compounds of the invention and the like.

A discussion of prodrugs may be found in "Smith and Williams' Introduction to the Principles of Drug Design," H. J. Smith, Wright, Second Edition, London (1988); Bundgard, H., *Design of Prodrugs* (1985), pp. 7-9, 21-24 (Elsevier, Amsterdam); The Practice of Medicinal Chemistry, Camille G. Wermuth et al., Ch 31, (Academic Press, 1996); A Textbook of Drug Design and Development, P. Krogsgaard-Larson and H. Bundgaard, eds. Ch 5, pgs 113 191 (Harwood Academic Publishers, 1991); Higuchi, T., et al., "Pro-drugs as Novel Delivery Systems," A.C.S. Symposium Series, Vol. 14; or in Bioreversible Carriers in Drug Design, ed. Edward B. Roche, American Pharmaceutical Association and Pergamon Press, 1987, all of which are incorporated in full by reference herein.

Suitable prodrug forms of the compounds of the invention include embodiments in which one of the hydroxyl groups is substituted with C(O)OR, where R is optionally substituted alkyl, alkenyl, alkynyl, aryl, or heteroaryl. In these cases the ester groups may be hydrolyzed in vivo (e.g. in bodily fluids), releasing the active compounds.

Conjugate compounds according to the invention, or for use according to the invention, can be provided alone or in combination with other compounds in the presence of a liposome, an adjuvant, or any pharmaceutically acceptable carrier, diluent or excipient, in a form suitable for administration to a subject such as a mammal, for example, humans, cattle, sheep, etc. If desired, treatment with a compound according to the invention may be combined with more traditional and existing therapies for the therapeutic indications described herein. Compounds according to the invention may be provided chronically or intermittently. "Chronic" administration refers to administration of the compound(s) in a continuous mode as opposed to an acute mode, so as to maintain the initial therapeutic effect (activity) for an extended period of time. "Intermittent" administration is treatment that is not consecutively done without interruption, but rather is cyclic in nature. The terms "administration," "administrable," or "administering" as used herein should be understood to mean providing a compound of the invention to the subject in need of treatment.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier that has been approved, for example, by the United States Food and Drug Administration or other governmental agency as being acceptable for use in humans or domestic animals.

The compounds of the present invention may be administered in the form of pharmaceutically acceptable salts. In such cases, pharmaceutical compositions in accordance with this invention may comprise a salt of such a compound, preferably a physiologically acceptable salt, which are known in the art. In some embodiments, the term "pharmaceutically acceptable salt" as used herein means an active ingredient comprising conjugate compounds used in the form of a salt thereof, particularly where the salt form confers on the active ingredient improved pharmacokinetic properties as compared to the free form of the active ingredient or other previously disclosed salt form.

A "pharmaceutically acceptable salt" includes both acid and base addition salts. A "pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

A "pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine,methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Thus, the term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or prodrug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

Pharmaceutical formulations will typically include one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The table or capsule may be enteric coated, or in a formulation for sustained release. Many suitable formulations are known, including, polymeric or protein microparticles encapsulating a compound to be released, ointments, gels, hydrogels, or solutions which can be used topically or locally to administer a compound. A sustained release patch or implant may be employed to provide release over a prolonged period of time. Many techniques known to skilled practitioners are described in *Remington: the Science & Practice of Pharmacy by Alfonso Gennaro*, 20$^{th}$ ed., Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The conjugate compounds or pharmaceutical compositions according to the present invention may be administered by oral or non-oral, e.g., intramuscular, intraperitoneal, intravenous, intracisternal injection or infusion, subcutaneous injection, transdermal or transmucosal routes. In some embodiments, conjugate compounds or pharmaceutical compositions in accordance with this invention or for use in this invention may be administered by means of a medical device or appliance such as an implant, graft, prosthesis, stent, etc. Implants may be devised which are intended to contain and release such compounds or compositions. An example would be an implant made of a polymeric material adapted to release the conjugate compound, or its individual components, over a period of time. The conjugate compounds may be administered alone or as a mixture with a pharmaceutically acceptable carrier e.g., as solid formulations such as tablets, capsules, granules, powders, etc.; liquid formulations such as syrups, injections, etc.; injections, drops, suppositories, pessaries. In some embodiments, conjugate compounds or pharmaceutical compositions in accordance with this invention or for use in this invention may be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The conjugate compounds of the invention may be used to treat animals, including mice, rats, horses, cattle, sheep, dogs, cats, and monkeys. However, compounds of the invention can also be used in other organisms, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the conjugate compounds, methods and pharmaceutical compositions of the present invention may be used in the treatment of animals. Accordingly, as used herein, a "subject" may be a human, non-human primate, rat, mouse, cow, horse, pig, sheep, goat, dog, cat, etc. The subject may be suspected of having or at risk for having a condition or disorder associated with abnormal or excessive bone loss, or with abnormal or reduced bone resorption, or with abnormal calcium metabolism, a cancer, a disorder associated with bone, or a disorder that would benefit from targeting a therapeutic agent to the bone.

An "effective amount" of a compound according to the invention includes a therapeutically effective amount or a prophylactically effective amount. A "therapeutically effective amount" refers to an amount effective, at dosages and for periods of time necessary, to achieve the desired therapeutic result, such as inhibition of bone resorption, stimulation of bone growth, or treatment of any condition described herein. A therapeutically effective amount of a compound may vary according to factors such as the disease state, age, sex, and weight of the individual, and the ability of the compound to elicit a desired response in the individual.

Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as inhibition of bone resorption, stimulation of bone growth, or prevention of any condition described herein. Typically, a prophylactic dose is used in subjects prior to or at an earlier stage of disease, so that a prophylactically effective amount may be less than a therapeutically effective amount. A suitable range for therapeutically or prophylactically effective amounts of a compound may be any value from 0.1 nM-0.1M, 0.1 nM-0.05M, 0.05 nM-15 µM or 0.01 nM-10 µM.

In alternative embodiments, in the treatment or prevention of conditions which require modulation of bone growth or resorption or calcium metabolism, an appropriate dosage level will generally be about 0.01 to 1000 mg per kg subject body weight per day, and can be administered in single or multiple doses. In some embodiments, the dosage level may be about 0.1 to about 250 mg/kg per day. In some embodiments, the dosage level may be about 5 mg/kg per day. In some embodiments, the dosage level may be such that leads to sustained release of the EP4 agonist or other agent at a rate of about 5 µg/kg per day to about 50 µg/kg per day, or about 15 µg/kg per day to about 25 µg/kg per day, or any value in between or inclusive of these ranges, such as about 5, 10, 15, 20, 25, 30, 35, 40, 45 or 40 µg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. In general, compounds of the invention should be used without causing substantial toxicity, and as described herein, the compounds exhibit a suitable safety profile for therapeutic use. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

In some embodiments, the conjugate compounds according to the invention are hydrolyzed at a rate that allows for dosage multiple times in a week.

In some embodiments, the conjugate compounds according to the invention are hydrolyzed at a rate that allows for dosage once a week.

In some embodiments, the conjugate compounds according to the invention are hydrolyzed at a rate that allows for dosage once a fortnight.

Various alternative embodiments and examples of the invention are described herein. These embodiments and examples are illustrative and should not be construed as limiting the scope of the invention.

The present invention will be further illustrated in the following examples.

EXAMPLES

Synthesis of C3-Conjugate 1

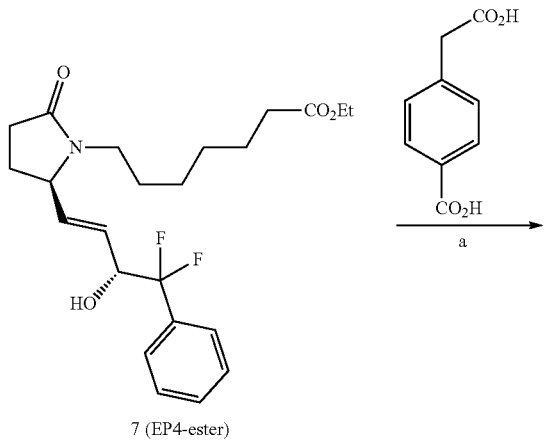

7 (EP4-ester)

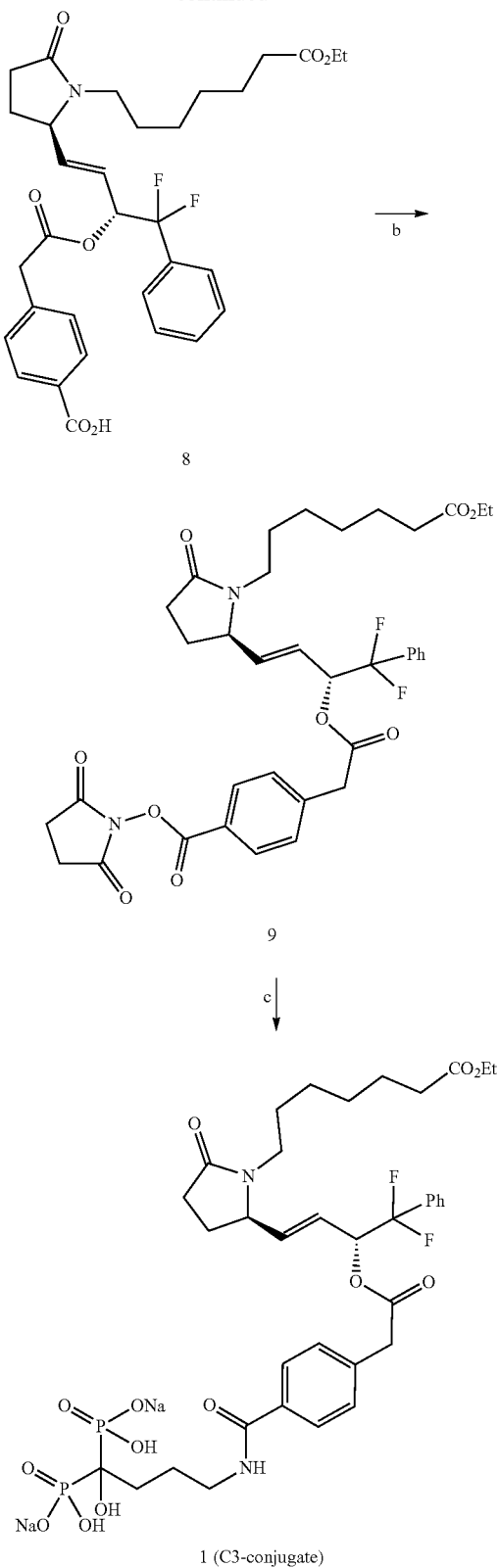

a) 4-(carboxymethyl)benzoic acid (1.6 equiv.), DCC (1.5 equiv.), DMAP (0.02 equiv.), pyridine (2.4 equiv.), CH$_2$Cl$_2$, rt, 2 h; b) N-hydroxysuccinimide (2.7 equiv.), EDCI (2.7 equiv.), DMF, rt, 7 h, 80% over two steps; c) Alendronic acid (4 equiv.), triethylamine (11.3 equiv.), DMF/H$_2$O (v/v) 2:1, rt, 10 min, 80%.

2,5-Dioxopyrrolidin-1-yl 4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzoate (9)

To a solution of EP4-ester 7 (0.200 g, 0.47 mmol, 1 equiv.) in dry CH$_2$Cl$_2$ (2.4 mL), were added 4-(carboxymethyl)benzoic acid (0.134 g, 0.75 mmol, 1.6 equiv.), DMAP (0.001 g, 0.01 mmol, 0.02 equiv.), pyridine (0.089 mL, 1.11 mmol, 2.4 equiv.) and then DCC (0.150 g, 0.73 mmol, 1.5 equiv.). The reaction mixture was allowed to stir under an argon atmosphere at room temperature for 2 h. The mixture was filtered and the filter cake was washed with MTBE. The filtrate was washed with a soslution of 0.5 M citric acid/water 1:1 (v/v). The aqueous layer was extracted three times with MTBE. The combined organic layers were dried over Na$_2$SO$_4$ and concentrated under reduced pressure in order to get acid 8. HRMS m/z calcd for C$_{32}$H$_{36}$F$_2$NO$_7$[M−H]$^-$ 584.2465, found 584.2469. The residue was solubilized in DMF (10 mL). To this solution, N-hydroxysuccinimide (0.147 g, 1.28 mmol, 2.7 equiv.) and N-(3-dimethylaminopropyl)-N'-ethylcarbodiimide hydrochloride (EDCl) (0.245 g, 1.28 mmol, 2.7 equiv.) were added. The reaction mixture was stirred for 7 h at room temperature under an argon atmosphere. The mixture was diluted with EtOAc and water. The aqueous layer was extracted three times with EtOAc. The combined organic layers were washed four times with a saturated aq. NaCl solution, dried over Na$_2$SO$_4$ and concentrated to dryness. The crude was then purified by flash chromatography (12 g BioTage HP Sil cartridge, 50% to 100% EtOAc/Hexane gradient) to give NHS-ester 9 (0.364 g, 80%) as colorless oil. $^1$H NMR (CDCl$_3$, 500 MHz) δ 8.03 (d, 2H, J=8.0 Hz), 7.45-7.32 (m, 5H), 7.27 (d, 2H, J=8.0 Hz), 5.74-5.68 (m, 1H), 5.64-5.54 (m, 2H), 4.09 (q, 2H, J=7.0 Hz), 4.03-3.98 (m, 1H), 3.72-3.63 (m, 2H), 3.46-3.40 (m, 1H), 2.93-2.82 (m, 4H), 2.65-2.58 (m, 1 H), 2.38-2.25 (m, 4H), 2.19-2.12 (m, 1H), 1.65-1.56 (m, 3H), 1.42-1.20 (m, 9H); $^{13}$C NMR (CDCl$_3$, 126 MHz) δ 174.7, 173.7, 169.3, 168.4, 161.5, 140.5, 138.1, 133.3 (t, J$_{C-F}$=31.7 Hz), 130.8, 130.6, 129.8, 128.4, 125.6 (t, J$_{C-F}$=7.6 Hz), 124.2, 123.7, 119.3 (t, J$_{C-F}$=299.0 Hz), 74.6 (t, J$_{C-F}$=40.8 Hz), 60.2, 59.6, 41.1, 40.4, 34.2, 29.8, 28.7, 27.0, 26.4, 25.7, 25.1, 24.8, 14.2; HRMS m/z calcd for C$_{36}$H$_{41}$F$_2$N$_2$O$_9$ [M+H]$^+$ 683.2775, found 683.2796; HPLC purity: 100%, t$_R$=3.0 min (Method 1).

Sodium (4-(4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxybutane-1,1-diyl)bis(hydrogen phosphonate) (C3-conjugate 1)

A stock solution of alendronic acid triethylammonium salt (pH ~10) was prepared by mixing alendronic acid (0.500 g, 2.01 mmol, 1 equiv.), water (3 mL), DMF (5 mL) and triethylamine (0.8 mL, 5.74 mmol, 2.85 equiv.).

To a solution of NHS-ester 9 (0.100 g, 0.15 mmol, 1 equiv.) in DMF (0.5 mL), was added the previously prepared stock solution of alendronic acid/Et$_3$N (2.6 mL; alendronic acid: 0.59 mmol, 4 equiv., triethylamine: 1.69 mmol, 11.3 equiv.). The reaction mixture was stirred at room temperature and monitored by HPLC. After 10 min stirring, the reaction was complete. The reaction was quenched with 0.1% formic acid in water. pH was adjusted to pH=6-7 with a 2% formic acid solution in water. The solution was then loaded onto an anion exchange column (1 g of Si-TMA Acetate Silicycle, loading: 0.94 mmol/g, packed in a SPE cartridge, activated by passing 0.1 M HCl/MeOH 1:1 (v/v), then 0.1% formic acid in water). It was sequentially eluted with 0.1% formic acid (3CV), MeOH/0.1% formic acid 1:1 (v/v) (3CV), MeOH (2CV) and MeOH/0.1 M HCl (5CV). This last acidic fraction was neutralized with 1 M NaOH and concentrated in vacuo to remove methanol. The remaining solution was loaded onto a 12 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v) in order to get, after freeze-drying, C3-conjugate 1 as a disodium salt (0.103 g, 80%) as a white solid. $^1$H NMR (D$_2$O, 600 MHz) δ 7.65 (d, 2H, J=9.0 Hz), 7.48 (t, 1H, J=7.2 Hz), 7.42-7.37 (m, 4H), 7.27 (d, 2H, J=7.8 Hz), 5.77-5.68 (m, 2H), 5.19-5.10 (m, 1H), 4.06 (m, 3H), 3.80 (d, 1H, J=15.0 Hz), 3.71 (d, 1H, J=15.0 Hz), 3.37 (t, 2H, J=7.2 Hz), 3.11-3.05 (m, 1H), 2.55-2.51 (m, 1H), 2.31-2.19 (m, 4H), 2.11-2.05 (m, 1H), 2.02-1.94 (m, 2H), 1.91-1.86 (m, 2H), 1.58-1.05 (m, 12H); $^{13}$C NMR (D$_2$O, 151 MHz) δ 177.3, 176.7, 171.1, 169.4, 136.8, 132.4, 131.9 (t, J$_{C-F}$=25.7 Hz), 130.4, 129.2, 128.0, 127.0, 125.5 (t, J$_{C-F}$=6.0 Hz), 123.6, 119.4 (t, J$_{C-F}$=249 Hz), 73.8 (t, J$_{C-F}$=33.2 Hz), 73.4, 61.1, 60.3, 40.3, 40.3, 40.2, 33.4, 30.6, 29.4, 27.1, 25.5, 25.0, 23.8, 23.6, 23.5, 23.1, 12.9; HRMS m/z calcd for C$_{36}$H$_{49}$F$_2$N$_2$O$_{13}$P$_2$ [M+H]$^+$ 817.2672, found 817.2692; HPLC purity: 100%, t$_R$=2.0 min (Method 1).

Synthesis of Double Radiolabelled C3-Conjugate [$^{14}$C/$^3$H]-1

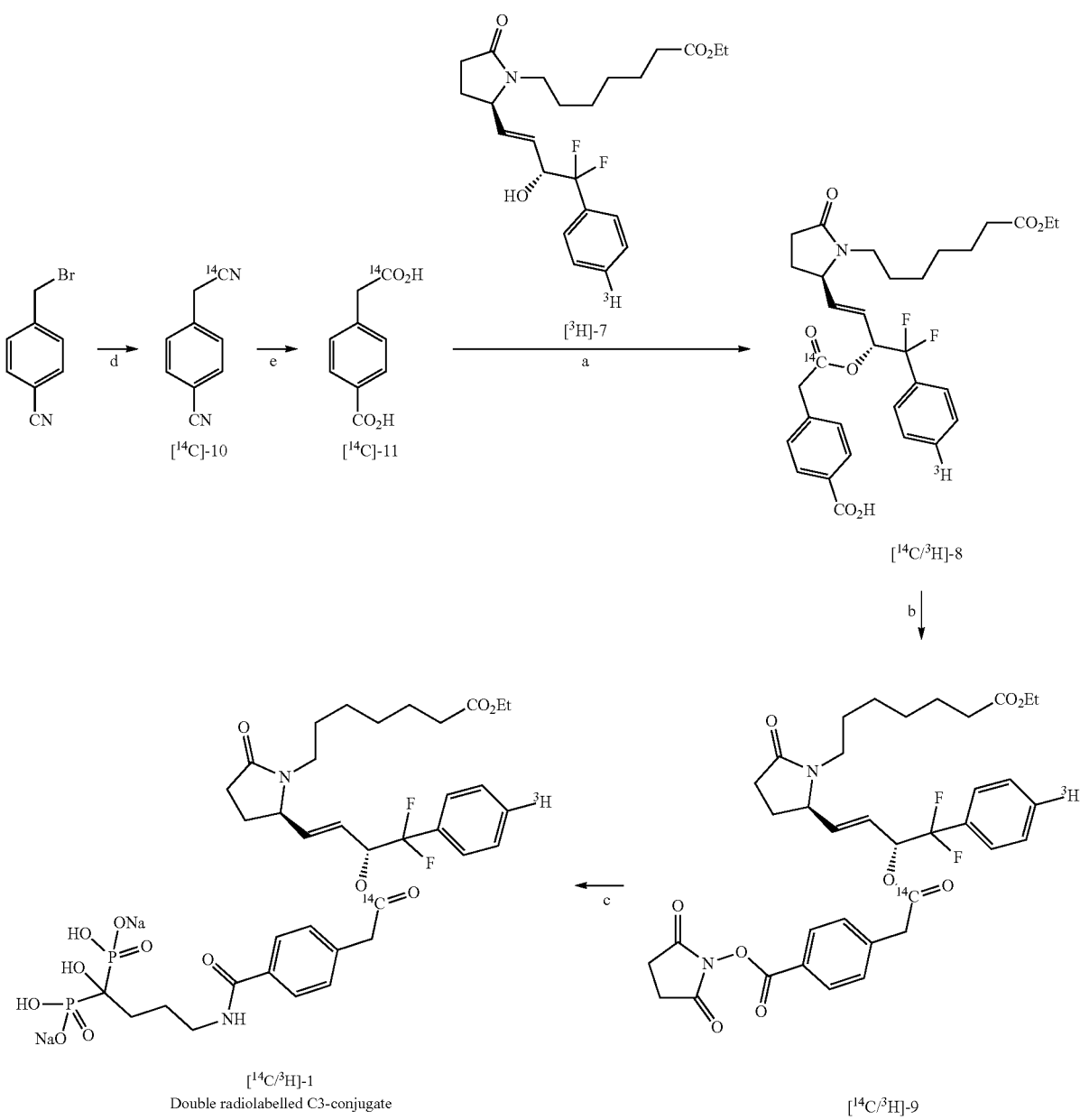

d) Na$^{14}$CN (0.33 equiv.), TBAB (0.17 equiv.), CH$_2$Cl$_2$/H$_2$O 1:1 (v/v), rt, overnight; e) i) 2M NaOH (2.8 equiv.), ii) HCl$_{conc.}$ The double radiolabeled C3-conjugate was synthesized following the same procedures used for unlabeled conjugate synthesis:

4-(cyanomethyl)benzonitrile (10)

A 4 mL vial was charged with tetrabutylammonium bromide (14 mg, 0.043 mmol, 0.5 equiv.) and sodium cyanide (4.2 mg, 0.085 mmol, 1 equiv.). After addition of dichloromethane (1.5 mL), water (1.5 mL) and 4-(bromomethyl)benzonitrile (0.050 g, 0.26 mmol, 3 equiv.), the phase-transfer reaction system was vigorously stirred overnight at room temperature. The aqueous phase was separated from the organic layer and extracted twice with $CH_2CL_2$. The combined organic layers were blown to dryness. The crude was columned through a Pasteur pipette charged with silica and eluted with 70% EtOAc/Hexane in order to yield 4-(cyanomethyl)benzonitrile (9.2 mg, 76%) as a colorless oil which solidifies into a white solid. The data were similar to that described in the literature (Velcicky, J.; Soicke, A.; Steiner, R.; Schmalz, H.-G. *J. Am. Chem. Soc.* 2011, 133, 6948-6951). $^1$H NMR ($CDCl_3$, 500 MHz) δ 7.70 (d, 2H, J=8.5 Hz), 7.48 (d, 2H, J=8.5 Hz), 3.84 (s, 2H); $^{13}$C NMR ($CDCl_3$, 151 MHz) δ 135.3, 133.0, 128.9, 118.2, 116.6, 112.5, 23.9; HPLC purity: 91%, $t_R$=1.9 min (Method 1).

4-(Carboxymethyl)benzoic Acid (11)

A mixture of 4-(cyanomethyl)benzonitrile (9.2 mg, 0.065 mmol) in an aqueous 2 M sodium hydroxide solution (0.9 mL, 2.8 equiv.) was stirred at 95° C. in a sealed tube for 2 h. The solution was cooled down to room temperature, transferred into a 1.5 mL Eppendorf® and acidified to pH 2 using concentrated hydrochloric acid. After cooling overnight at 4° C. (refrigerator), crystals were formed. The mixture was centrifuged (8000 rpm, 1 min). The supernatant was removed and replaced with water. The mixture was centrifuged again and water was removed. This procedure was repeated three times to wash the precipitate. The wet solid was dried under vacuum in order to yield 4-(carboxymethyl)benzoic acid (5.3 mg, 46%) as a white solid. The data were similar to that described in the literature (Huh, D. H.; Jeong, J. S.; Lee, H. B.; Ryu, H.; Kim, Y. G. *Tetrahedron* 2002, 58, 9925-9932). $^1$H NMR (acetone-$d_6$, 500 MHz) δ 8.00 (d, 2H, J=8.5 Hz), 7.46 (d, 2H, J=8.5 Hz), 3.74 (s, 2H); $^{13}$C NMR (acetone-$d_6$, 151 MHz) δ 172.2, 167.5, 141.2, 130.5, 130.5, 130.1, 41.2; HRMS m/z calcd for $C_9H_9O_4$ $[M+H]^+$ 181.0495, found 181.0494.

Steps a) to c) were previously described for cold C3-conjugate 1

Synthesis of Acid C3-Conjugate

Sodium (4-(4-(2-(((R,E)-4-((R)-1-(6-carboxyhexyl)-5-oxopyrrolidin-2-yl)-1,1-difluoro-1-phenylbut-3-en-2-yl)oxy)-2-oxoethyl)benzamido)-1-hydroxybutane-1,1-diyl)bis(hydrogen phosphonate)

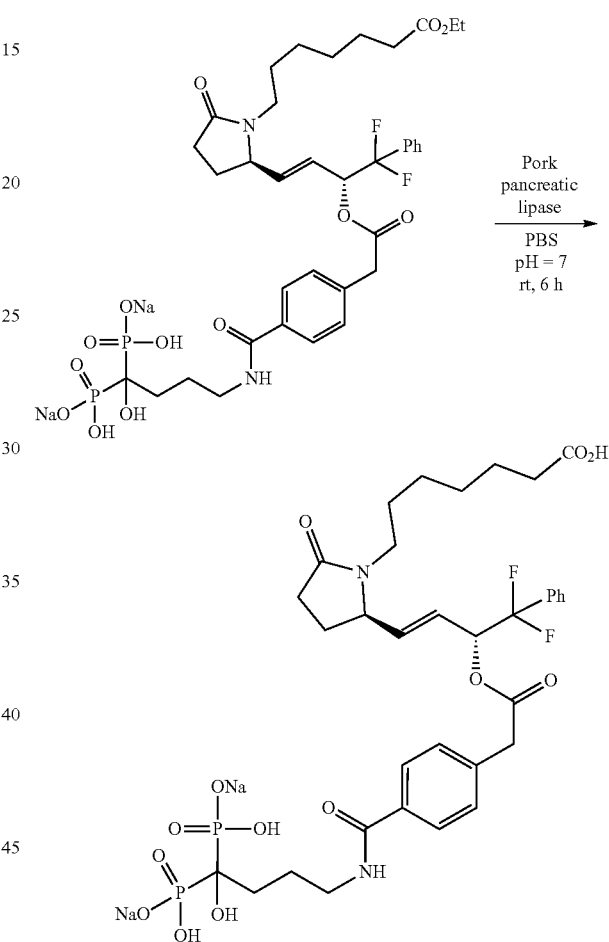

To a solution of C3-conjugate disodium salt (0.189 g, 0.22 mmol) in phosphate buffered saline (pH=7), pork pancreatic lipase (washed beforehand with acetone) (0.567 g) was added. The reaction mixture was stirred at room temperature for 6 h and directly loaded onto a 12 g C18 RP-chromatography column (activated by MeOH, then water) using as gradient: 1.5 CV of water, 12 CV gradient 0% to 100% MeOH/$H_2O$, 3CV 100% MeOH and 3CV MeOH/$H_2O$ 1:1 (v/v). Four peaks were observed, the third and larger one was collected and concentrated to get few milliliters of a colorless solution, frozen and lyophilized for three days in order to give sodium (4-(4-(2-(((R,E)-4-((R)-1-(6-carboxyhexyl)-5-oxopyrrolidin-2-yl)-1,1-difluoro-1-phenylbut-3-en-2-yl)oxy)-2-oxoethyl)benzamido)-1-hydroxybutane-1,1- diyl)bis(hydrogen phosphonate) (0.037 g, 20%) as a white solid. $^1$H NMR (D$_2$O, 500 MHz) δ 7.71 (d, 2H, J=8.1 Hz), 7.54 (t, 1H, J=6.8 Hz), 7.48-7.43 (m, 4H), 7.34 (d, 2H, J=8.1 Hz), 5.88-5.74 (m, 2H), 5.14 (dd, 1H, J=14.9, 8.9 Hz), 4.19-4.14 (m, 1H), 3.87 (d, 1H, J=15.0 Hz), 3.78 (d, 1H, J=15.1 Hz), 3.44-3.41 (m, 2H), 3.26-3.16 (m, 1H), 2.56-2.47 (m, 1H), 2.39-2.21 (m, 2H), 2.16 (t, 2H, J=7.5 Hz), 2.06-1.98 (m, 4H), 1.56-1.07 (m, 10H); $^{13}$C NMR (D$_2$O, 151 MHz) δ 183.5, 177.3, 171.2, 169.6, 136.8, 135.7, 132.4, 131.9 (t, $J_{C-F}$=24.8 Hz), 130.3, 129.3, 128.0, 127.0, 125.5 (t, $J_{C-F}$=5.59 Hz), 123.5, 119.4 (t, $J_{C-F}$=247 Hz), 73.9 (t, $J_{C-F}$=32.6 Hz), 60.0, 40.3, 40.3, 37.0, 30.8, 29.4, 27.9, 27.1, 25.6, 25.3, 23.7, 23.4, 23.2; HRMS m/z calcd for C$_{34}$H$_{45}$F$_2$N$_2$O$_{13}$P$_2$ [M+H]$^+$798.2359, found 798.2367; HPLC purity: 96%, $t_R$=1.7 min (Method 1).

Synthesis of C4-conjugate 2

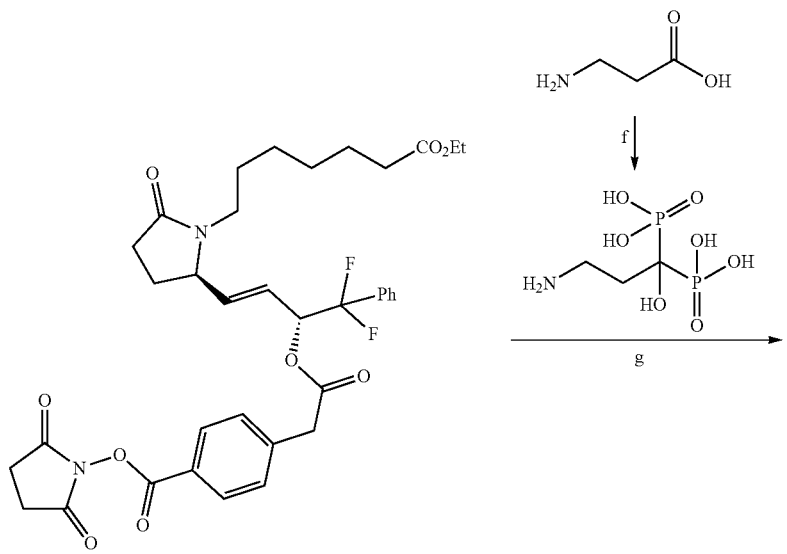

9

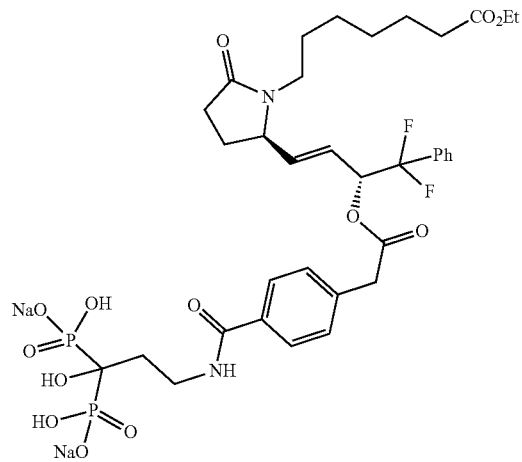

2 (C4-conjugate)

f) i) Phosphorous acid (1 equiv.), PCl$_3$ (2.1 equiv.), CH$_3$SO$_3$H, 65° C. to 70° C., overnight, 99%, ii) H$_2$O, 0° C. to reflux, 5 h then aq. 1N NaOH, iii) Si-tosic acid exchange column;
g) Pamidronic acid (4 equiv.), triethylamine (11 equiv.), DMF/H$_2$O (v/v) 2:1, rt, 30 min, 60%.

(3-Amino-1-hydroxypropane-1,1-diyl)bis(phosphonic acid) (pamidronic acid)

A mixture of 3-aminopropionic acid (1.00 g, 11.2 mmol, 1 equiv.) and phosphorous acid (0.920 g, 11.2 mmol, 1 equiv.) in methanesulfonic acid (4.7 mL) was heated at 65° C. Phosphorus trichloride (2.06 mL, 23.6 mmol, 2.1 equiv.) was added slowly under stirring. After completion of the addition, the temperature was raised to 70° C. and the reaction mixture was stirred overnight under an argon atmosphere at the same temperature. The clear, colorless solution was cooled to 25° C. and quenched at 0-5° C. with water (4 mL) under vigorous stirring. The mixture was then refluxed for 5 h. The solution was cooled to 20° C. and the pH was adjusted to 2 with 1 N sodium hydroxide solution. Methanol was added to the mixture and a precipitate was formed. The mixture aged overnight at 4° C. The precipitate was filtered off and washed with methanol. The white solid was then solubilized in water and loaded onto a cation exchange column (Si-Tosic acid 40-63 μm, 0.55 mmol/g) which was beforehand rinsed with 100% MeOH and then 100% water. It was eluted with water and the resulting solution was then freeze-dried to get pamidronic acid as a free acid (2.619 g, 99%) as a white solid. $^1$H NMR (D$_2$O, 400 MHz) δ 3.30 (t, 2H, J=6.9 Hz), 2.33-2.22 (m, 2H); $^{13}$C NMR (D$_2$O, 151 MHz) δ 71.7 (t, J$_{C-P}$=140 Hz), 35.3 (t, J$_{C-P}$=7.40 Hz), 30.0; $^{31}$P NMR (D$_2$O, 162 MHz) δ 17.6; HRMS m/z calcd for C$_3$H$_{12}$NO$_7$P$_2$ [M+H]$^+$ 236.0084, found 236.0081.

Sodium (3-(4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyp benzamido)-1-hydroxypropane-1,1-diyl)bis(hydrogen phosphonate) (C4-conjugate 2)

A stock solution of pamidronic acid triethylammonium salt (pH ~10) was prepared by mixing pamidronic acid (0.500 g, 2.13 mmol, 1 equiv.), water (3 mL), DMF (5 mL) and triethylamine (0.8 mL, 5.74 mmol, 2.70 equiv.).

To a solution of NHS-ester 9 (0.050 g, 0.07 mmol, 1 equiv.) in DMF (0.25 mL), was added the previously prepared stock solution of pamidronic acid/Et$_3$N (1.3 mL; pamidronic acid: 0.30 mmol, 4 equiv., triethylamine: 0.81 mmol, 11 equiv.). The reaction mixture was directly loaded onto a 12 g C18 RP-chromatography column (activated by MeOH, then water, gradient: 1.5 CV of water, 10 CV gradient 0% to 100% MeOH/H$_2$O, 3CV 100% MeOH and 3CV MeOH/H2O 1:1 (v/v)) to give C4-conjugate triethylammonium salt. This latter was loaded onto a cation exchange column (0.32 g Si-Tosic acid 40-63 μm, 0.68 mmol/g) which was beforehand rinsed with 100% MeOH, 100% water and 5% aq. NaCl solution. The column was washed with MeOH/H$_2$O 1:1 (v/v). The collected solution (pH 7) was concentrated in vacuo to remove methanol and loaded onto a 12 g C18 RP chromatography (activated by MeOH, then water, gradient: 1.5 CV of water, 10 CV gradient 0% to 100% MeOH/H$_2$O, 3CV 100% MeOH and 3CV MeOH/H$_2$O 1:1 (v/v) to give, after freeze-drying, C4-conjugate 2 as a disodium salt (0.040 g, 60%) as a white solid. $^1$H NMR (D$_2$O, 600 MHz) δ 7.75 (d, 2H, J=7.8 Hz), 7.57-7.55 (m, 1H), 7.48-7.43 (m, 4H), 7.33 (d, 2H, J=7.8 Hz), 5.84-5.80 (m, 1H), 5.77 (dd, 1H, J=15.0, 6.0 Hz), 5.28 (dd, 1 H, J=15.0, 9.0 Hz), 4.15-4.11 (m, 3H), 3.86 (d, 1 H, J=15.0 Hz), 3.79-3.74 (m, 2H), 3.19-3.14 (m, 1H), 2.65-2.61 (m, 1H), 2.38-2.26 (m, 6H), 2.19-2.13 (m, 1H), 1.58-1.46 (m, 3H), 1.36-1.15 (m, 10H); $^{13}$C NMR (D$_2$O, 151 MHz) δ 177.3, 176.6, 171.0, 168.9, 136.7, 136.0, 132.4, 131.9 (t, J$_{C-F}$=25.1 Hz), 130.4, 129.2, 128.0, 127.0, 125.4 (t, J$_{C-F}$=5.9 Hz), 123.6, 119.4 (t, J$_{C-F}$=248 Hz), 73.9 (t, J$_{C-F}$=32.6 Hz), 72.6 (t, J$_{C-F}$=132 Hz), 61.0, 60.3, 40.3, 40.2, 35.8 (t, J$_{C-F}$=7.9 Hz), 33.4, 32.4, 29.4, 27.2, 25.5, 25.0, 23.8, 23.6, 12.9; HRMS m/z calcd for C$_{35}$H$_{47}$F$_2$N$_2$O$_{13}$P$_2$ [M+H]$^+$ 803.2514, found 803.2516; HPLC purity: 100%, t$_R$=2.1 min (Method 1).

Synthesis of C5-conjugate 3

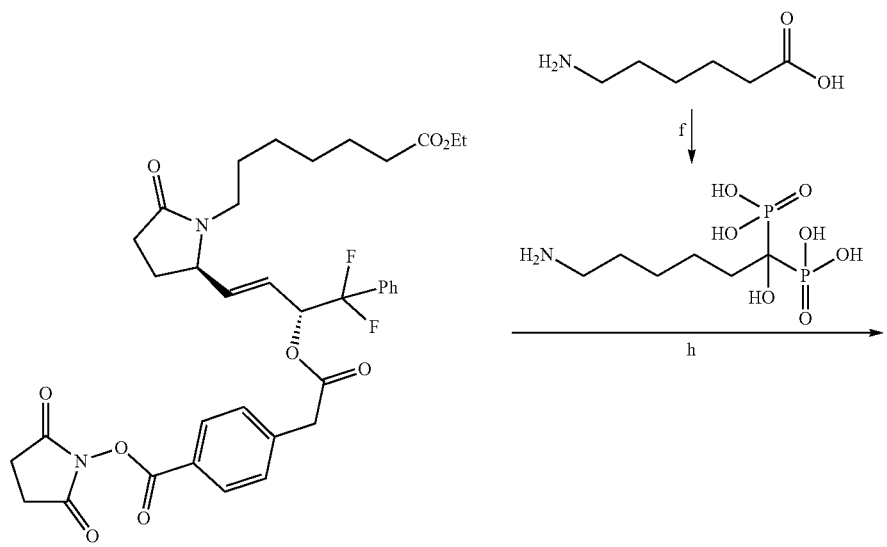

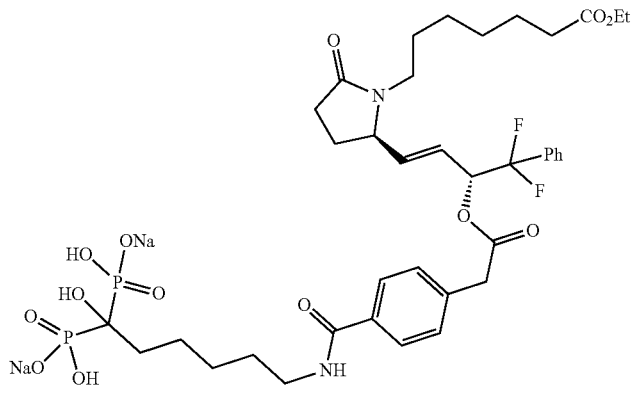

3 (C5-conjugate)

f) i) Phosphorous acid (1 equiv.), PCl₃ (2.1 equiv.), CH₃SO₃H, 65° C. to 70° C., overnight, 47%, ii) H₂O, 0° C. to reflux, 5 h then aq. 1N NaOH, iii) Si-tosic acid exchange column;
h) Pamidronic acid (4 equiv.), triethylamine (13 equiv.), DMF/H₂O (v/v) 2:1, rt, 30 min, 60%.

(6-Amino-1-hydroxyhexane-1,1-diyl)bis(phosphonic acid) (neridronic acid)

A mixture of 3-aminohexanoic acid (0.500 g, 3.81 mmol, 1 equiv.) and phosphorous acid (0.313 g, 3.81 mmol, 1 equiv.) in methanesulfonic acid (1.6 mL) was heated at 65° C. under an inert atmosphere. Phosphorus trichloride (0.67 mL, 8.00 mmol, 2.1 equiv.) was added slowly under stirring. After completion of the addition, the temperature was raised to 70° C. and the reaction mixture was stirred overnight under an argon atmosphere at the same temperature. The clear, colorless solution was cooled down to 25° C. and quenched into 0-5° C. with water (4 mL) under vigorous stirring. The mixture was then refluxed for 5 h. The solution was cooled down to 20° C. and the pH was adjusted to 2 with 1 N sodium hydroxide solution. Methanol was added to the mixture and a precipitate was formed. The mixture aged overnight at 4° C. The precipitate was filtered off and washed with methanol. The white solid was then solubilized in water and loaded onto a cation exchange column (Si-Tosic acid 40-63 μm, 0.55 mmol/g) which was rinsed with 100% MeOH and then 100% water. It was eluted with water and the resulting solution was then freeze-dried to get neridronic acid as a free acid (0.500 g, 47%) as a white solid. $^1$H NMR (D₂O, 500 MHz) δ 3.00 (t, 2H, J=7.4 Hz), 1.93 (m, 2H), 1.72-1.66 (m, 2H), 1.64-1.58 (m, 2H), 1.43-1.37 (m, 2H); $^{13}$C NMR (D₂O, 126 MHz) δ 74.1 (t, $J_{C\text{-}P}$=134.8 Hz), 39.3, 33.4, 26.3, 26.2, 22.9 (t, $J_{C\text{-}P}$=6.3 Hz); $^{31}$P NMR (D₂O, 162 MHz) δ 19.3; HRMS m/z calcd for C₆H₁₈NO₇P₂ [M+H]⁺ 278.0553, found 278.0566.

(Sodium (6-(4-(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxyhexane-1,1-diyl)bis(hydrogen phosphonate) (C5-conjugate 3)

A stock solution of neridronic acid triethylammonium salt (pH ~10) was prepared by mixing neridronic acid (0.500 g, 1.80 mmol, 1 equiv.), water (3 mL), DMF (5 mL) and triethylamine (0.8 mL, 5.74 mmol, 3.19 equiv.).

To a solution of NHS-ester 9 (0.050 g, 0.07 mmol, 1 equiv.) in DMF (0.25 mL), was added the previously prepared stock solution of neridronic acid/Et₃N (1.4 mL; pamidronic acid: 0.29 mmol, 4 equiv., triethylamine: 0.91 mmol, 13 equiv.). The reaction mixture was directly loaded onto a 12 g C18 RP-chromatography column (activated by MeOH, then water, gradient: 1.5 CV of water, 10 CV gradient 0% to 100% MeOH/H₂O, 3CV 100% MeOH and 3CV MeOH/H₂O 1:1 (v/v)) to give C4-conjugate triethylammonium salt. This latter was loaded onto a cation exchange column (0.32 g Si-Tosic acid 40-63 μm, 0.68 mmol/g) which was beforehand rinsed with 100% MeOH, 100% water and 5% aq. NaCl solution. The column was washed with MeOH/H₂O 1:1 (v/v). The collected solution (pH 7) was concentrated in vacuo to remove methanol and loaded onto a 12 g C18 RP chromatography (activated by MeOH, then water, gradient: 1.5 CV of water, 10 CV gradient 0% to 100% MeOH/H₂O, 3CV 100% MeOH and 3CV MeOH/H₂O 1:1 (v/v) to give, after freeze-drying, C5-conjugate 3 as a disodium salt (0.034 g, 55%) as a white solid. $^1$H NMR (D₂O, 500 MHz) δ 7.68 (d, 2H, J=8.0 Hz), 7.55-7.52 (m, 1H), 7.48-7.42 (m, 4H), 7.33 (d, 2H, J=8.0 Hz), 5.82-5.73 (m, 2H), 5.13-5.08 (m, 1H), 4.14-4.10 (m, 3H), 3.87 (d, 1H, J=15.0 Hz), 3.76 (d, 1H, J=15.0 Hz), 3.45-3.35 (m, 2H), 3.15-3.10 (m, 1H), 2.59-2.54 (m, 1H), 2.37-2.10 (m, 5H), 1.99-1.91 (m, 2H), 1.70-1.62 (m, 4H), 1.56-1.51 (m, 2H), 1.44-1.40 (m, 3H), 1.34-1.28 (m, 1H), 1.24-1.10 (m, 8H); $^{13}$C NMR (D₂O, 151 MHz) δ 176.9, 175.8, 170.3, 168.6, 136.6, 136.5, 132.4, 132.2 (t, $J_{C\text{-}F}$=25.2 Hz), 130.3, 129.1, 128.0, 126.9, 125.3 (t, $J_{C\text{-}F}$=5.6 Hz), 123.6, 119.3 (t, $J_{C\text{-}F}$=248 Hz), 73.8 (t, $J_{C\text{-}F}$=33.0 Hz), 73.8 (t, $J_{C\text{-}F}$=134 Hz), 60.8, 60.2, 40.2, 40.0, 39.6, 33.4, 33.1, 29.4, 28.0, 27.4, 26.7, 25.7, 25.2, 23.9, 23.7, 22.8, 13.0; HRMS m/z calcd for C₃₈H₅₃F₂N₂O₁₃P₂ [M+H]⁺845.2985, found 845.2971; Purity: 100%, tR=2.1 min (Method 1).

Synthesis of C3 fragment 4 and C4 fragment 5

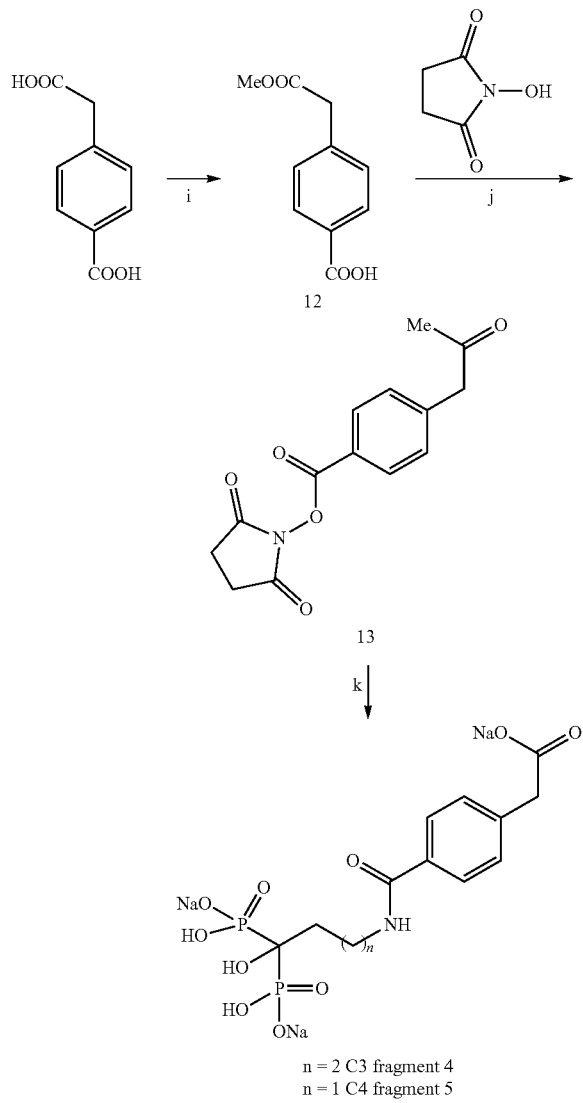

n = 2 C3 fragment 4
n = 1 C4 fragment 5 i) SOCl$_2$ (5 mol %), MeOH, rt, overnight, 91%; j) NHS (2.7 equiv.), EDCI (2.7 equiv.), DMF, rt, 3.5 h, 97%; k) i) Alendronic acid or pamidronic acid (4 equiv.), Et$_3$N (11.8 equiv.), DMF/H$_2$O 2:1 (v/v), rt, 30 min, 71%, ii) 1M NaOH (4 equiv.)/H$_2$O 1:1 (v/v), rt, overnight, 55%.

4-(2-Methoxy-2-oxoethyl)benzoic acid (12)

To a solution of 4-(carboxymethyl)benzoic acid (1.00 g, 5.55 mmol, 1 equiv.) in methanol (11 mL), were added thionyl chloride (0.020 mL, 0.28 mmol, 5 mol %). The reaction mixture was stirred overnight at room temperature. The solvent was evaporated under reduced pressure and the residual material was taken up in MTBE and washed successively three times with a saturated aq. NaHCO$_3$ solution and once with water. The combined bicarbonate and aqueous extract was acidified with 1 N HCl until precipitation of the monomethyl ester. The mixture was extracted three times with MTBE. The combined organic layers were dried over Na$_2$SO$_4$ and concentrated under reduced pressure in order to get 4-(2-methoxy-2-oxoethyl)benzoic acid 12 (0.985 g, 91%) as a white solid. $^1$H NMR (CDCl$_3$, 400 MHz) δ 8.08 (d, 2H, J=8.4 Hz), 7.40 (d, 2H, J=8.4 Hz), 3.72 (s, 5H). The data were similar to that described in WO2005/12220.

2,5-Dioxopyrrolidin-1-yl 4-(2-methoxy-2-oxoethyl)benzoate (13)

To a solution of monoacid 12 (0.917 g, 4.72 mmol, 1 equiv.) in DMF (107 mL), N-hydroxysuccinimide (1.47 g, 12.8 mmol, 2.7 equiv.) and N-(3-dimethylamino-propyl)-N-ethylcarbodiimide hydrochloride (2.44 g, 12.8 mmol, 2.7 equiv.) were added. The reaction mixture was stirred at room temperature for 3.5 h under an argon atmosphere. The colorless mixture was diluted with EtOAc and water. The solution was extracted three times with EtOAc. The combined organic layers were washed three times with water, dried over Na$_2$SO$_4$ and concentrated under reduced pressure in order to get NHS-ester 13 (1.329 g, 97%) as a pale yellow oil. $^1$H NMR (CDCl$_3$, 600 MHz) δ 8.10 (d, 2H, J=8.1 Hz), 7.44 (d, 2H, J=8.1 Hz), 3.72 (s, 2H), 3.71 (s, 3H), 2.90 (s, 4H); $^{13}$C NMR (CDCl$_3$, 151 MHz) δ 169.9, 168.3, 160.8, 140.5, 130.0, 129.0, 123.2, 51.5, 40.4, 24.8; C$_{14}$H$_{14}$NO$_6$ [M+H]$^+$292.0816, found 292.0824; C$_{14}$H$_{17}$N$_2$O$_6$ [M+NH$_4$]$^+$ 309.1081, found 309.1084; Purity: 100%, t$_R$=2.4 min.

Sodium 2-(4-((4-hydroxy-4,4-bis(hydroxyoxidophosphoryl)butyl)carbamoyl)phenyl)acetate (C3 fragment 4)

A stock solution of alendronic acid triethylammonium salt (pH ~10) was prepared by mixing alendronic acid (1.00 g, 4.02 mmol, 1 equiv.), water (6 mL), DMF (10 mL) and triethylamine (1.6 mL, 11.5 mmol, 2.85 equiv.).

To a solution of NHS-ester 13 (0.200 g, 0.69 mmol, 1 equiv.) in DMF (1 mL), was added the previously prepared stock solution of alendronic acid/Et$_3$N (12.5 mL; alendronic acid: 2.86 mmol, 4 equiv., triethylamine: 8.17 mmol, 11.8 equiv.). The reaction mixture was stirred at room temperature and monitored by HPLC. After 30 min stirring, the reaction was complete. The reaction was quenched with 0.1% formic acid in water. pH was adjusted to pH=6-7 with a 2% formic acid solution in water. The solution was then loaded onto an anion exchange column (6.2 g of Si-TMA Acetate Silicycle, loading: 1.16 mmol/g, packed in a SPE cartridge, activated by passing 0.1 M HCl/MeOH 1:1 (v/v), then 0.1% formic acid in water). It was sequentially eluted with 0.1% formic acid (3CV), MeOH/0.1% formic acid 1:1 (v/v) (3CV), MeOH (2CV) and MeOH/0.1 M HCl (5CV). This last acidic fraction was neutralized with 1 M NaOH and concentrated in vacuo to remove methanol. The remaining solution was loaded onto a 12 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v) in order to get intermediate methyl ester C3 fragment. $^1$H NMR (D$_2$O, 600 MHz) δ 7.77 (d, 2H, J=8.4 Hz), 7.44 (d, 2H, J=8.4 Hz), 3.85 (s, 2H), 3.74 (s, 3H), 3.45 (t, 2H, J=6.0 Hz), 2.06-2.05 (m, 2H); 1.99-1.95 (m, 2H); $^{13}$C NMR (D$_2$O, 151 MHz) δ 174.4, 170.2, 137.3, 132.4, 129.2, 127.0, 126.8, 52.2, 40.2, 39.7, 30.6, 23.1; C$_{14}$H$_{22}$NO$_{10}$P$_2$ [M+H]$^+$ 426.0713, found 426.0701.

To a solution of intermediate methyl ester C3 fragment in water (about 3 mL) was added a 1 M NaOH aqueous solution (2.7 mL, 2.74 mmol, 4 equiv.). The reaction mixture was stirred overnight at room temperature. 1 N HCl was added to neutralize pH. The mixture was then loaded onto a 25 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v) to yield after freeze-drying C3 fragment 4 as a trisodium salt (0.310 g, 95%) as a white solid. $^1$H NMR (D$_2$O, 600 MHz) δ 7.74 (d, 2H, J=8.1 Hz), 7.40 (d, 2H, J=8.1 Hz), 3.62 (s, 2H), 3.44 (t, 2H, J=6.7 Hz), 2.19-1.79 (m, 4H); $^{13}$C NMR (D$_2$O, 151 MHz) δ 179.8, 170.4, 140.9, 131.5, 128.9, 126.8, 73.4 (t, $J_{C-P}$=132 Hz), 43.9, 40.3, 30.9, 23.2 (t, $J_{C-P}$=6.1 Hz); C$_{13}$H$_{20}$NO$_{10}$P$_2$ [M+H]$^+$412.0557, found 412.0568; Purity: 100%.

Sodium2-(4-((3-hydroxy-3,3-bis(hydroxyoxidophosphoryl)propyl)carbamoyl)phenyl)acetate (C4 fragment 5)

A stock solution of pamidronic acid triethylammonium salt (pH ~10) was prepared by mixing pamidronic acid (0.500 g, 2.13 mmol, 1 equiv.), water (3 mL), DMF (5 mL) and triethylamine (0.8 mL, 5.74 mmol, 2.70 equiv.).

To a solution of NHS-ester 13 (0.050 g, 0.17 mmol, 1 equiv.) in DMF (0.25 mL), was added the previously prepared stock solution of alendronic acid/Et$_3$N (2.9 mL; alendronic acid: 0.70 mmol, 4 equiv., triethylamine: 2.00 mmol, 11.8 equiv.). The reaction mixture was stirred at room temperature and monitored by HPLC. After 30 min stirring, the reaction was complete. The reaction was quenched with 0.1% formic acid in water. pH was adjusted to pH=6-7 with a 2% formic acid solution in water. The solution was then loaded onto an anion exchange column (1.22 g of Si-TMA Acetate Silicycle, loading: 1.16 mmol/g, packed in a SPE cartridge, activated by passing 0.1 M HCl/MeOH 1:1 (v/v), then 0.1% formic acid in water). It was sequentially eluted with 0.1% formic acid (3CV), MeOH/0.1% formic acid 1:1 (v/v) (3CV), MeOH (2CV) and MeOH/0.1 M HCl (5CV). This last acidic fraction was neutralized with 1 M NaOH and concentrated in vacuo to remove methanol. The remaining solution was loaded onto a 12 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v) in order to get intermediate methyl ester C4 fragment. $^1$H NMR (D$_2$O, 400 MHz) δ 7.75 (d, 2H, J=8.1 Hz), 7.41 (d, 2H, J=8.1 Hz), 3.82 (s, 2H), 3.74-3.67 (m, 5H), 2.41-2.21 (m, 2H); C$_{13}$H$_{20}$NO$_{10}$P$_2$ [M+H]$^+$412.0557, found 412.0566. To a solution of ester C4 fragment in water (about 1 mL) was added a 1 M NaOH aqueous solution (0.7 mL, 0.68 mmol, 4 equiv.). The reaction mixture was stirred overnight at room temperature. 1 N HCl was added to neutralize pH. The mixture was then loaded onto a 4 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v) to yield after freeze-drying, C4 fragment 5 as a trisodium salt (0.056 g, 71%). $^1$H NMR (D$_2$O, 600 MHz) δ 7.77 (d, 2H, J=8.0 Hz), 7.41 (d, 2H, J=8.0 Hz), 3.73 (t, 2H, J=7.5 Hz), 3.62 (s, 2H), 2.35-2.16 (m, 2H); $^{13}$C NMR (D$_2$O, 151 MHz) δ 179.8, 169.8, 140.9, 131.5, 128.9, 126.8, 72.6 (t, $J_{C-P}$=128 Hz), 43.9, 36.0 (t, $J_{C-P}$=8.1 Hz), 32.5; C$_{12}$H$_{18}$NO$_{10}$P$_2$ [M+H]$^+$ 398.0400, found 398.0407; Purity: 100%.

Synthesis of Amide-Linked C3 Conjugate Bearing Two EP4 Agonists

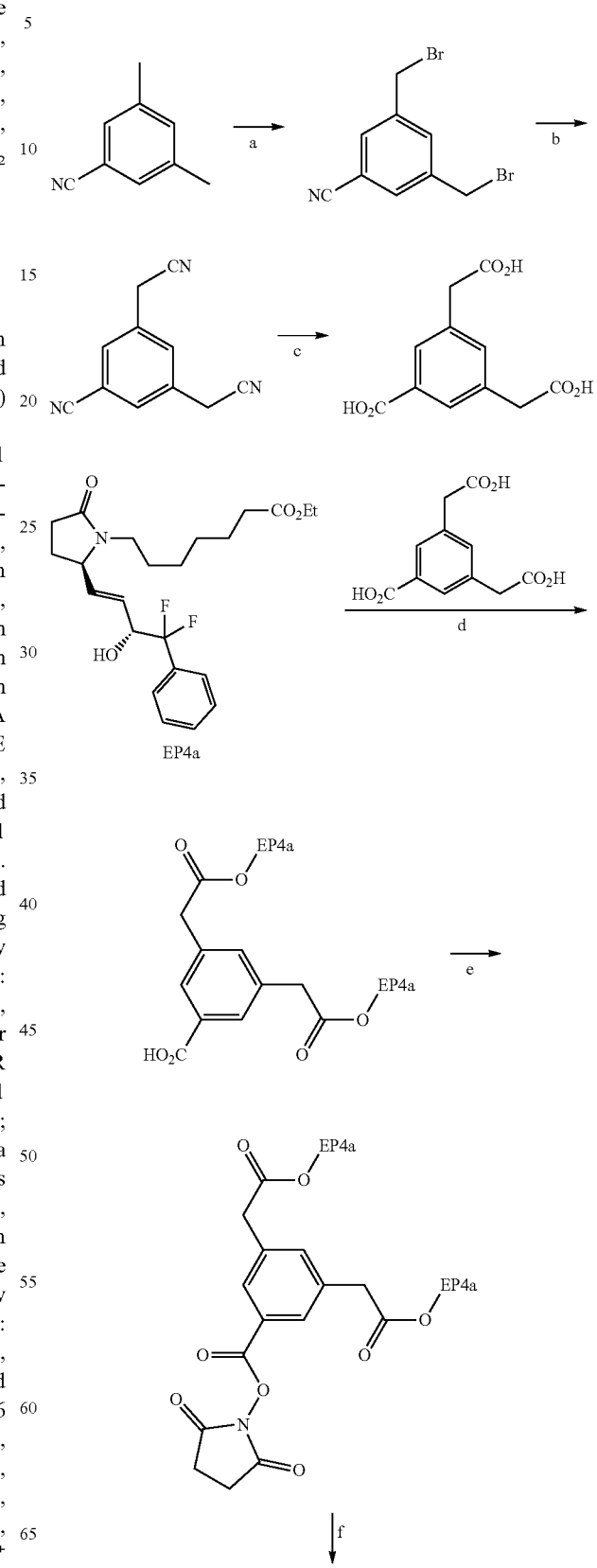

-continued

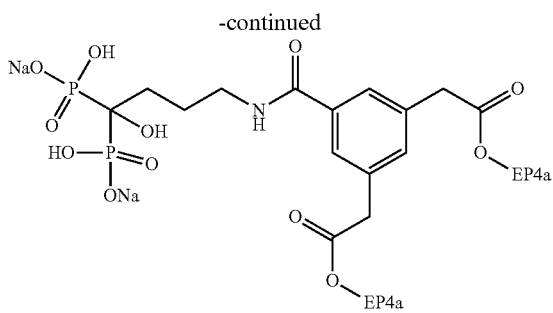

3,5-Bis(bromomethyl)benzonitrile

To a solution of 3,5-dimethylbenzonitrile (1.00 g, 7.62 mmol, 1 euiv.) in 1,2-dichloroethane (76 mL), were added N-bromosuccinimide (2.98 g, 16.8 mmol, 2.2 equiv.) and azobisisobutyronitrile (0.250 g, 1.52 mmol, 0.2 equiv.). The reaction mixture was stirred under an argon atmosphere for 9 h at 80° C. $H_2O$ was added to the medium which was extracted three times with $CH_2Cl_2$. The combined organic layers were washed with brine, dried over $Na_2SO_4$ and concentrated under reduced pressure. The residue was purified by flash chromatography (25 g BioTage HP Sit cartridge, 2% to 15% EtOAc/Hexane gradient, 20 CV) to yield 3,5-bis(bromomethyl)benzonitrile (0.618 g, 28%) as white crystals. Similar data as described in literature. $^1$H NMR (CDCl$_3$, 500 MHz) δ 7.64 (s, 1H), 7.61 (d, 2H, J=1.2 Hz), 4.45 (s, 4H); HPLC purity: 99%, $t_R$=2.9 min (Method 1). Similar data as described in literature (Easson, M. W.; Fronczek, F. R.; Jensen, T.; Vicente, M. G. H. Bioorg. Med. Chem. 2008, 16, 3191-3208).

2,2'-(5-Cyano-1,3-phenylene)diacetonitrile

To a solution of 3,5-bis(bromomethyl)benzonitrile (0.581 g, 2.01 mmol, 1 equiv.) in a mixture of $CH_2Cl_2/H_2O$ 1:1 (v/v) (30 mL), were added tetrabutylammonium bromide (0.648 g, 2.01 mmol, 1 equiv.) and sodium cyanide (0.207 g, 4.22 mmol, 2.1 equiv.). The phase-transfer reaction system was vigorously stirred overnight at room temperature. The aqueous phase was separated from the organic layer and extracted three times with DCM. The combined organic layers (included the one from the reaction mixture) were concentrated under reduced pressure. The crude was purified by flash chromatography (12 g BioTage HP Sit cartridge, 15% to 50% EtOAc/Hexane gradient) to yield 2,2'-(5-cyano-1,3-phenylene)diacetonitrile (0.215 g, 59%) as white crystals. $^1$H NMR (CDCl$_3$, 400 MHz) δ 7.65-7.64 (m, 2H), 7.60-7.59 (m, 1 H), 3.85 (s, 4H); $^{13}$C NMR (CDCl$_3$, 101 MHz) δ 133.0, 132.0, 131.3, 117.2, 116.4, 114.5, 23.4; HRMS m/z calcd for $C_{11}H_7N_3Na$ [M+Na]$^+$204.0532, found 204.0542; HPLC purity: 100%, $t_R$=1.6 min (Method 1).

2,2'-(5-Carboxy-1,3-phenylene)diacetic Acid

A mixture of 2,2'-(5-cyano-1,3-phenylene)diacetonitrile (0.215 g, 1.19 mmol, 1 equiv.) in an aqueous 2 M sodium hydroxide solution (15 mL, 30.0 mmol, 25 equiv.) was heated to reflux for 4 h. Upon cooling the solution was acidified to pH 2 using concentrated hydrochloric acid. The solution was extracted three times with EtOAc. The combined organic layers were dried over $Na_2SO_4$ and concentrated under reduced pressure in order to yield 2,2'-(5-carboxy-1,3-phenylene)diacetic acid (0.283 g, quant.) as a white solid. $^1$H NMR (Acetone-d$_6$, 400 MHz) δ 7.92 (d, 2H, J=1.6 Hz), 7.52 (t, 1H, J=1.6 Hz), 3.74 (s, 4H); $^{13}$C NMR (DMSO, 101 MHz) δ 172.5, 167.2, 135.5, 135.0, 130.8, 128.8, 21.1; HRMS m/z calcd for $C_{11}H_9O_6$ [M+H]$^+$ 237.0405, found 204.0536.

Diethyl 7,7'-((5R,5'R)-((1E,1'E,3R,3'R)-((2,2'-(5-(((2,5-dioxopyrrolidin-1-yl)oxy)carbonyl)-1,3-phenylene)bis(acetyl))bis(oxy))bis(4,4-difluoro-4-phenylbut-1-ene-3,1-diyl))bis(2-oxopyrrolidine-5,1-diyl))diheptanoate To a solution of EP4 agonist ethyl 7-((R)-2-((R,E)-4,4-difluoro-3-hydroxy-4-phenylbut-1-en-1-yl)-5-oxopyrrolidin-1-yl)heptanoate (0.356 g, 0.84 mmol, 2 equiv.) and 2,2'-(5-carboxy-1,3-phenylene)diacetic acid (0.100 g, 0.42 mmol, 1 equiv.) in distilled dichloromethane (2 mL), were successively added pyridine (0.159 mL, 1.97 mmol, 4.7 equiv.), DMAP (0.002 g, 0.02 mmol, 0.04 equiv.) and then DCC (0.260 g, 1.26 mmol, 3 equiv.). The reaction mixture was stirred under nitrogen at room temperature for 3 h and then concentrated to dryness. The residue was solubilized with MTBE and the mixture was filtered through Celite®. The filter cake was washed with MTBE. The filtrate was washed with a solution of 0.5 M citric acid/water 1:1 (v/v). The aqueous layer was extracted twice with MTBE. The combined organic layers were dried over $Na_2SO_4$ and concentrated under reduced pressure in order to give 3,5-bis(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl) benzoic acid as colorless oil and used for the next step without any further purification.

The crude (0.440 g, 0.42 mmol, 1 equiv.) was dissolved in DMF (9 mL). To this solution, were added N-hydroxysuccinimide (0.386 g, 3.36 mmol, 8 equiv.) and N-(3-dimethylamino-propyl)-N-ethylcarbodiimide hydrochloride (EDCl) (0.643 g, 3.36 mmol, 8 equiv.). The reaction mixture was stirred overnight at room temperature under an argon atmosphere. The resulting red solution was diluted with water and EtOAc. The aqueous layer was extracted four times with EtOAc. The combined organic layers were washed four times with a saturated aq. NaCl solution, dried over $Na_2SO_4$ and concentrated to dryness. The crude was then purified by flash chromatography (12 g BioTage HP Sil cartridge, 0% to 15% MeOH/$CH_2Cl_2$ gradient, 20 CV) followed by a second flash chromatography (12 g BioTage HP Sil cartridge, 90% to 100% AcOEt/Hexane gradient, 20 CV and then 1% to 15% MeOH/EtOAc gradient, 20CV) to yield diethyl 7,7'-((5R,5'R)-((1E,1'E,3R,3'R)-((2,2'-(5-(((2,5-dioxopyrrolidin-1-yl)oxy)carbonyl)-1,3-phenylene)bis(acetyl))bis(oxy))bis(4,4-difluoro-4-phenylbut-1-ene-3,1-diyl))bis(2-oxopyrrolidine-5,1-diyl))diheptanoate (0.265 g, 55%) as a pale pink oil. $^1$H NMR (CDCl$_3$, 400 MHz) δ 7.80 (s, 2H), 7.45-7.25 (m, 11H), 5.80-5.46 (m, 6H), 4.07 (q, 4H, J=7.1 Hz), 4.00-3.95 (m, 2H), 3.73-3.55 (m, 4H), 3.46-3.30 (m, 2H), 2.88 (s, 4H), 2.58-2.51 (m, 2H), 2.33-2.21 (m, 8H), 2.17-2.05 (m, 2H), 1.65-1.52 (m, 6H), 1.40-1.16 (m, 18H); $^{13}$C NMR (CDCl$_3$, 101 MHz) δ 174.7, 173.6, 169.2, 168.5, 161.2, 138.0, 136.7, 134.5, 133.2 (t, $J_{C-F}$=37.9 Hz), 130.5, 130.1, 128.3, 125.9, 125.5 (t, $J_{C-F}$=9.5 Hz), 123.7, 119.2 (t, $J_{C-F}$=373 Hz), 74.5 (t, $J_{C-F}$=47.1 Hz), 60.1, 59.6, 40.3, 40.3, 34.1, 29.7, 28.6, 26.9, 26.3, 25.6, 25.0, 24.7, 14.1; HRMS m/z calcd for $C_{61}H_{72}F_4N_3O_{14}$ [M+H]$^+$1146.4945, found 1146.4918; HPLC purity: 97%, $t_R$=1.7 min (Method 2).

Sodium (4-(3,5-bis(2-(((R,E)-4-((R)-1-(7-ethoxy-7-oxoheptyl)-5-oxopyrrolidin-2-yl)-1,1-difluoro-1-phenyibut-3-en-2-ypoxy)-2-oxoethyl)benzamido)-1-hydroxybutane-1,1-diyl)bis(hydrogen phosphonate)

A stock solution of alendronic acid triethylammonium salt (pH ~10) was prepared by mixing alendronic acid (0.500 g, 2.01 mmol, 1 equiv.), water (3 mL), DMF (5 mL) and triethylamine (0.8 mL, 5.74 mmol, 2.85 equiv.).

To a solution of diethyl 7,7'-((5R,5'R)-((1E,1'E,3R,3'R)-((2,2'-(5-(((2,5-dioxopyrrolidin-1-yl)oxy)carbonyl)-1,3-phenylene)bis(acetyl))bis(oxy))bis(4,4-difluoro-4-phenyl-but-1-ene-3,1-diyl))bis(2-oxopyrrolidine-5,1-diyl)) diheptanoate (0.025 g, 0.022 mmol, 1 equiv.) in DMF (0.25 mL), was added was added the previously prepared stock solution of alendronic acid/Et$_3$N (0.78 mL; alendronic acid: 0.18 mmol, 8 equiv., triethylamine: 0.51 mmol, 23 equiv.). The reaction mixture was stirred at room temperature and monitored by HPLC. After 1.5 h, the solution was diluted 6-8 fold with 0.1% formic acid in water and finally, neutralized with a 2% formic acid solution to get a neutral pH which was loaded onto an anion exchange column (0.6 g of Si-TMA Acetate Silicycle, loading: 0.94 mmol/g, activated by passing MeOH, 0.1 M HCl/MeOH 1:1 (v/v), then 0.1% formic acid in water). It was sequentially eluted with 0.1% formic acid (5CV), MeOH/0.1% formic acid 1:1 (v/v) (5CV), MeOH (3CV) and MeOH/0.1 M HCl (7CV). 1 M NaOH was added to the fractions of this last acid phase to increase pH to 7. The mixture was concentrated under reduced pressure to remove methanol and get a smaller volume of solution which was loaded onto a 12 g C18 RP-chromatography column (activated by MeOH, then water) using as gradient: 1.5 CV of water, 12 CV gradient 0% to 100% MeOH/H$_2$O, 3CV 100% MeOH and 3CV MeOH/H$_2$O 1:1 (v/v). One peak was observed, collected and concentrated to get few milliliters of a colorless solution which was frozen and lyophilized for 48 h in order to give sodium (4-(3,5-bis(2-(((R,E)-4-((R)-1-(7-ethoxy-7-oxoheptyl)-5-oxopyrrolidin-2-yl)-1,1-difluoro-1-phenylbut-3-en-2-yl)oxy)-2-oxoethyl)benzamido)-1-hydroxybutane-1,1-diyl) bis(hydrogen phosphonate) (0.013 g, 46%) as a white solid. $^1$H NMR (D$_2$O, 500 MHz) δ 7.57 (s, 2H), 7.39-7.30 (m, 10H), 6.95 (s, 1H), 5.78-5.73 (m, 2H), 5.59 (dd, 2H, J=14.7, 6.8 Hz), 5.48 (dd, 2H, J=14.7, 9.0 Hz), 4.01 (q, 4H, J=6.7 Hz), 3.92-3.91 (m, 2H), 3.67 (d, 2H, J=15.5 Hz), 3.60 (d, 2H, J=15.5 Hz), 3.37 (s, 2H), 3.10 (s, 2H), 2.49 (s, 2H), 2.29 (s, 4H), 2.20-2.18 (m, 4H), 2.04-1.92 (m, 6H), 1.54-1.39 (m, 6H), 1.27-1.01 (m, 18H); $^{13}$C NMR (D$_2$O, 151 MHz) δ 176.7, 174.9, 169.8, 167.8, 137.6, 134.4, 133.6, 132.6 (t, $J_{C-F}$=27.2 Hz), 132.4, 130.2, 128.0, 126.8, 125.2, 123.5, 119.3 (t, $J_{C-F}$=247.6 Hz), 74.0 (t, $J_{C-F}$=31.7 Hz), 60.4, 60.2, 40.3, 40.1, 39.8, 33.4, 30.6, 29.3, 27.6, 25.8, 25.4, 24.0, 23.8, 23.2, 13.1); HRMS m/z calcd for C$_{61}$H$_{78}$F$_4$N$_3$O$_{18}$P$_2$ [M–H]$^-$ 1278.4697, found 1278.4692; HPLC purity: 98%, $t_R$=2.5 min (Method 1).

Biological Evaluation

Stability of Conjugate Compounds in Rat Plasma

The amide-linked conjugate compounds were examined for their stability in rat plasma. Each [$^3$H]-labelled molecule (tritium labeling on the EP4 agonist (from compound 8) portion of the molecule) corresponding to conjugate compounds 1, 2 and 3 (C3, C4 and C5 respectively) was added to a solution of unlabelled conjugate compound in fresh rat plasma in order to get an activity of 500,000 dpm and 100 µg/mL concentration. The mixture was then incubated at 37° C. for 24 h. Aliquots of 10 µL were removed at 0, 2, 4, 6, 7 and 24 h, mixed to 10 mg of bone powder and 10-fold diluted with water in a 0.6 mL Eppendorf tube. A gentle stirring was applied for 20 min. 50 µL were then used to count the activity.

At the initial time points, about 90% of each conjugate compound was found to be taken up into bone powder (FIG. 1). About 10% hydrolysis was noted after 24 h-incubation in the case of the C3-conjugate compound whereas less than 5% hydrolysis was found with other two conjugate compounds (C4 or C5). Accordingly, the amide linked-conjugate compounds were determined to be relatively stable over 24 hours.

In Vivo Uptake Studies of C3, C4 and C5-Conjugates 6 Hours after Dosing

Figure 2:
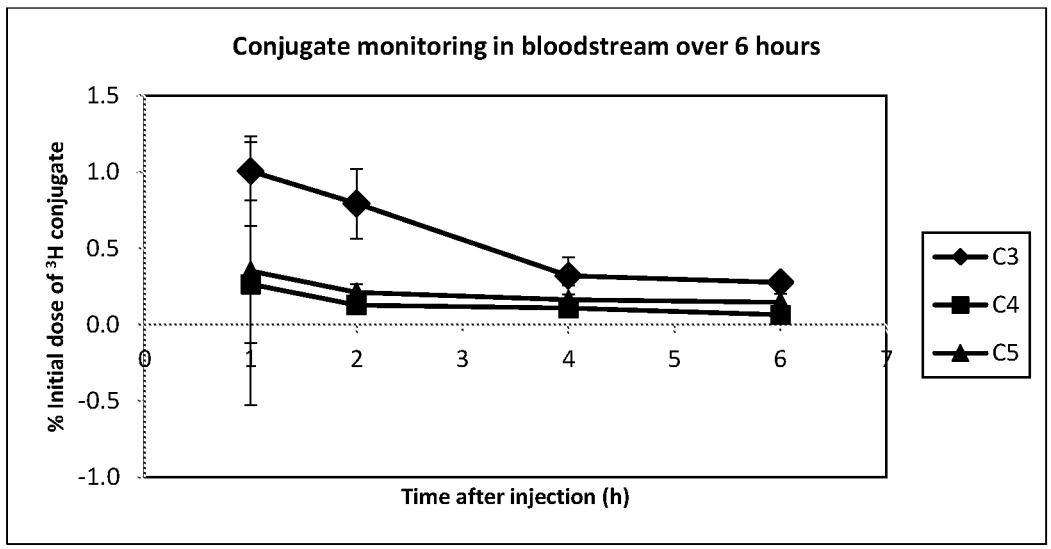
FIG. 2 is a graph showing the release of labelled conjugates into the bloodstream of rats over 6 hours.

The three conjugate compounds, C3, C4 and C5, were radiolabelled with tritium in the EP4 agonist moiety and used to monitor in vivo distribution in rat organs and uptake into bone after intravenous dosing. All three conjugate compounds tested on a 3-rat group were well tolerated (dosed at 1-5 µCi/5 mg/kg) and radioactivity was shown to be rapidly cleared from plasma (FIG. 2).

Figure 3:
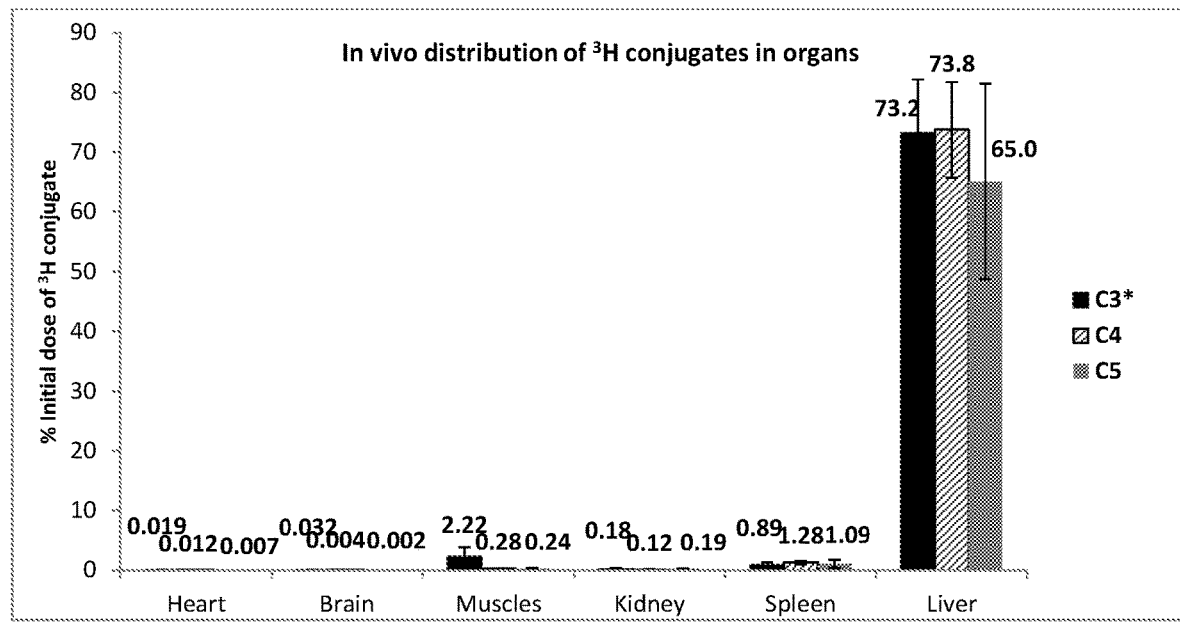
FIG. 3 is a graph showing the distribution of labelled C3, C4 and C5-conjugates in rat organs 6 h after dosing.

The radioactivity in organs (heart, kidney, brain, muscle, one piece of muscle attached to bone, spleen and liver) was counted 6 hours after dosing (FIG. 3). For the C3-conjugate compound, calculations were done based on results obtained from two rats. Most of the labelled conjugate compounds were taken up into liver (65-74%), and about 1% and 0.2% were found in spleen and kidneys for all labelled conjugate compounds, after 6 hours. About 0.2% of the initial dose of the C4 and C5-conjugate compounds, and 2% of the C3-conjugate compound, was found in muscle. All other organs contained 0.05% of the initial dose of the conjugate compounds.

Figure 4:
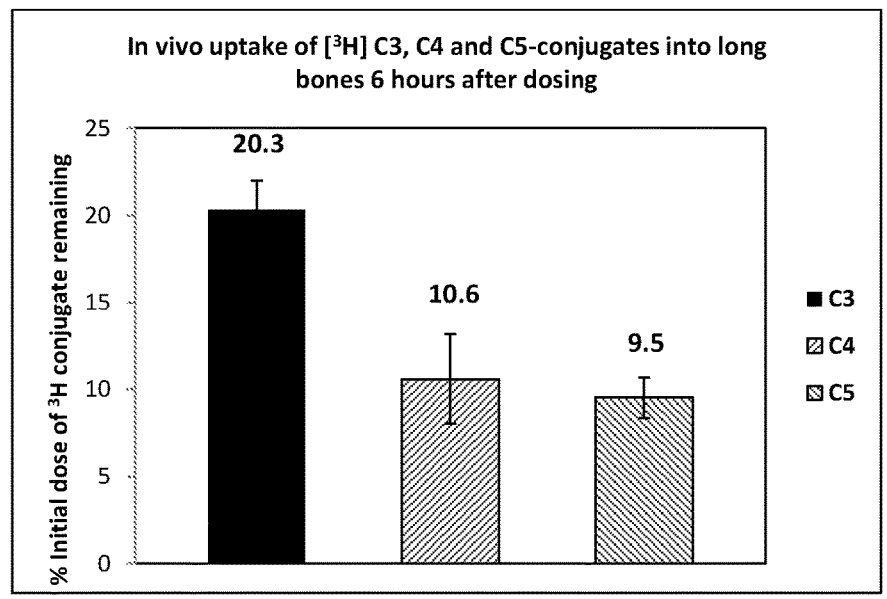
FIG. 4 is a graph showing the uptake of tritium labelled conjugates into rat long bones 6 hours after dosing.

Finally, the uptake of the tritiated C3, C4 and C5-conjugate compounds into bones was counted (FIG. 4). All three conjugate compounds were well taken up into bone. C4 and C5-conjugate compounds with a pamidronate and a neridronate moiety, respectively, showed about 10% uptake into long bones. About 20% of C3-conjugate compound, with an alendronate moiety, was found to be attached to bone 6 hours after injection (based on results obtained from two rats).

Figure 5:
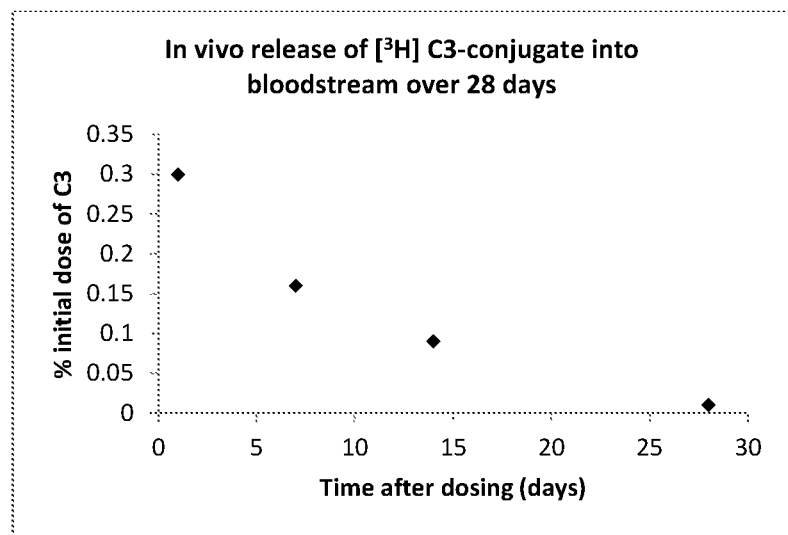
FIG. 5 is a graph showing the release of tritium labelled C3-conjugate into rat bloodstream over 28 days.
Figure 6:
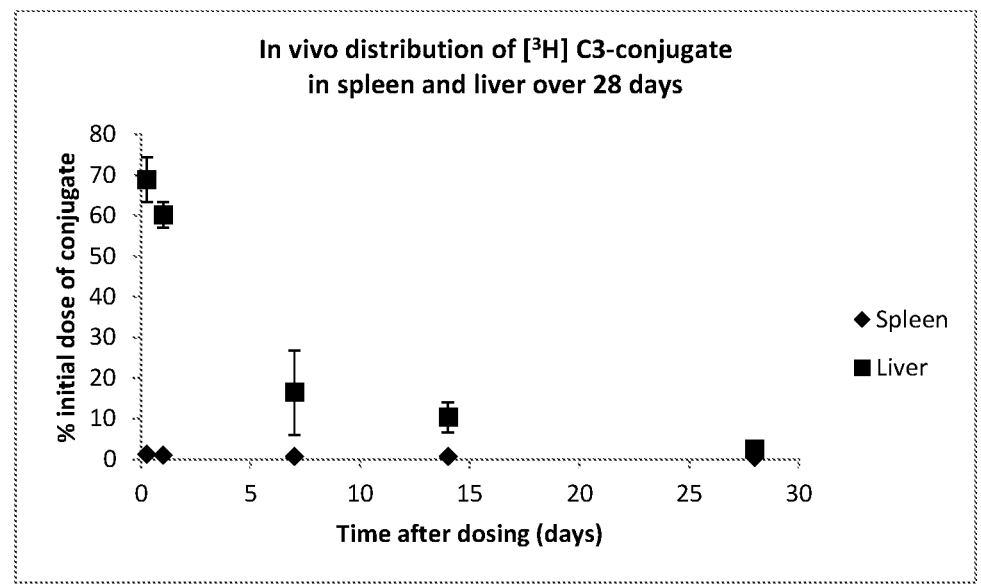
FIG. 6 is a graph showing the distribution of tritium labelled C3-conjugate in rat spleen and liver over 28 days.
Figure 7:
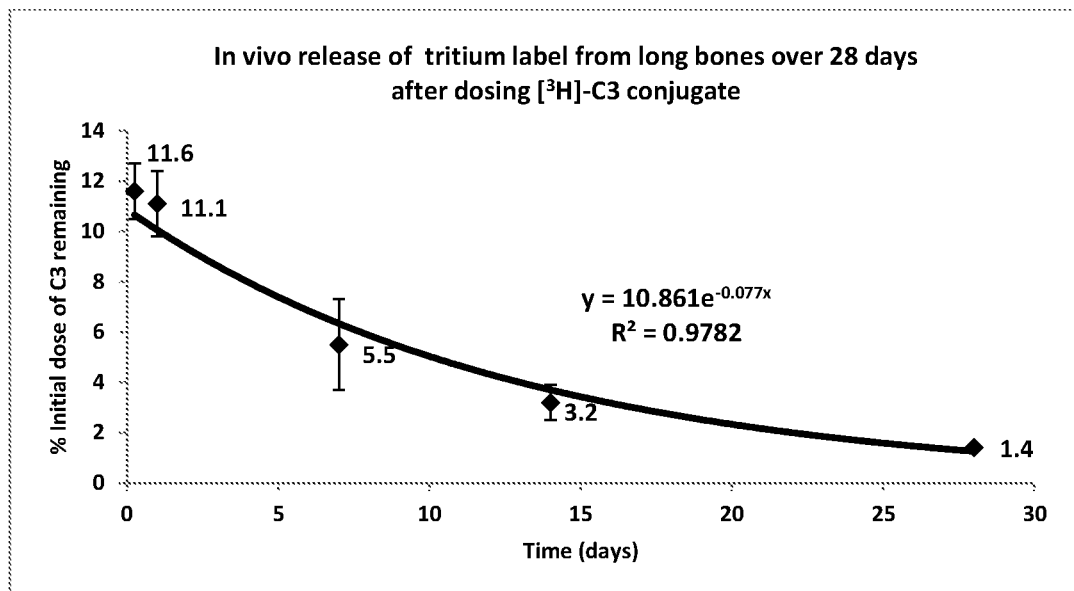
FIG. 7 is a graph showing the release of tritium labelled C3-conjugate from rat long bones over 28 days.

In Vivo Uptake and Release Studies of Tritium Labelled C3-Conjugate Over 28 Days As the C3-conjugate compound was found to attach well to bone, it was used in a long-term study of over 28 days. In vivo uptake and release studies using tritium labelled C3-conjugate compound were performed. After intravenous dosing of 1-5 µCi/5 mg/kg of [$^3$H]-C3 to 15 rats, groups of 3 rats were euthanized at each time point a at t=6 h, 24 h, 7 d, 14 d, 28 d). The radioactivity in blood samples, spleen, liver and long bones was counted for each group of rats. Very low activity was detected in the bloodstream, indicating a rapid clearance of the tritiated C3-conjugate compound from plasma (FIG. 5). Most of the tritiated C3-conjugate compound (69%) was found in liver 6 hours after injection and remained in a high proportion after 24 hours. After one week, 53% of label was eliminated and only traces were detected after 28 days (FIG. 6). In spleen, the counted radioactivity decreased from 1% 6 hours after dosing to 0.4% at t=28 days (FIG. 6). The tritiated C3-conjugate compound exhibited about 12% uptake to bone after 6 hours (FIG. 7). After 7 days, 5.5% of the tritiated C3-conjugate compound remained attached to bone, whereas 1.4% of the initial dose was observed in bone at the end of the study. Based on these results, a half-life of about 8 days was calculated.

In Vivo Uptake and Release Studies of Double Radiolabelled C3-Conjugate Over 28 Days A double-radiolabelled molecule with tritium in the EP4 agonist portion and $^{14}C$ in the linker connected to the bisphosphonate moiety:

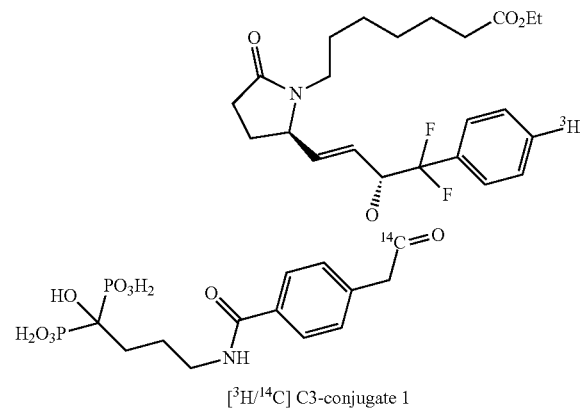

[$^3H/^{14}C$] C3-conjugate 1 was used to monitor in vivo uptake into bone and the subsequent release of both elements in a rat model.

Figure 9:
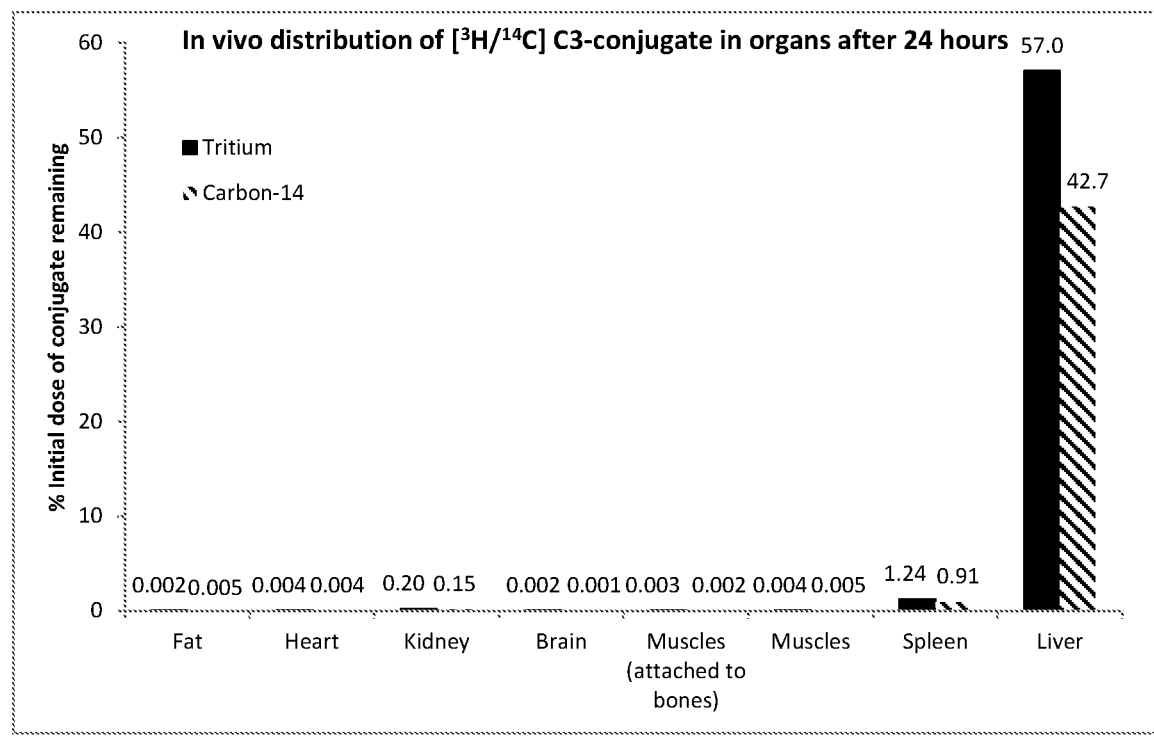
FIG. 9 is a graph showing the distribution of double labelled C3-conjugate in rat organs 24 h after dosing.

Double-labelled C3-conjugate compound (dosed at 1-5 µCi for each label/5 mg/kg) was well tolerated and clearance from plasma of radioactivity over 28 days was observed (FIGS. 8A and 8B). The radioactivity in organs (fat, heart, kidneys, brain, muscle, one piece of muscle attached to bone, spleen and liver) was counted 24 hours after dosing (FIG. 9). Half of the labelled conjugate was taken up into liver (57% and 43% for tritium and $^{14}C$ labels, respectively) and about 1% and 0.2% was found in spleen and kidneys for both labels after 24 hours. All other organs analysed in this study contained ≥0.004% of the initial dose of double-labelled conjugate compound.

Figure 10:
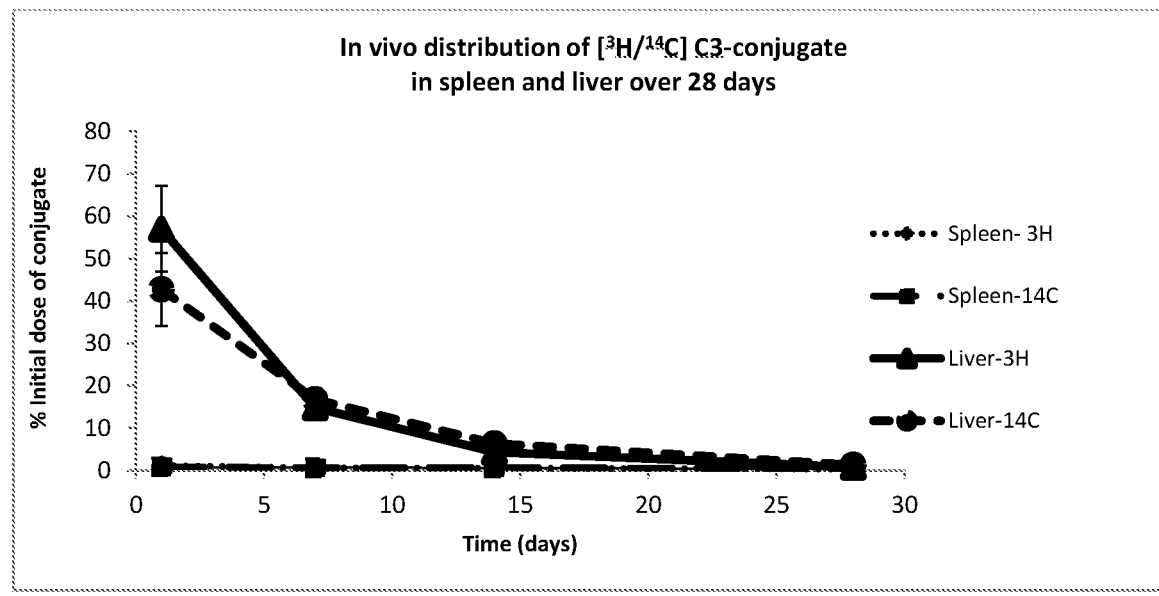
FIG. 10 is a graph showing the distribution of radioactivity in rat spleen and liver, after dosing the double labelled C3-conjugate, over 28 days.

Radioactivity in spleen and liver was counted, as shown in FIG. 10 and Table 1.

TABLE 1

Distribution data of the double labelled C3-conjugate radioactivity in rat spleen and liver over 28 days

| Time | % Initial tritium dose of conjugate | | | | % Initial carbon-14 dose of conjugate | | | |
|---|---|---|---|---|---|---|---|---|
| | Spleen | | Liver | | Spleen | | Liver | |
| (d) | Mean | ±SD | Mean | ±SD | Mean | ±SD | Mean | ±SD |
| 1 | 1.2 | 0.25 | 57 | 10.1 | 0.91 | 0.2 | 42.7 | 8.6 |
| 7 | 0.66 | 0.11 | 14.8 | 2 | 0.65 | 0.1 | 16.8 | 2.6 |
| 14 | 0.58 | 0.17 | 4.3 | 0.71 | 0.69 | 0.2 | 6.4 | 1.7 |
| 28 | 0.34 | 0.21 | 0.78 | 0.53 | 0.4 | 0.25 | 1.3 | 0.85 |

Figure 11:
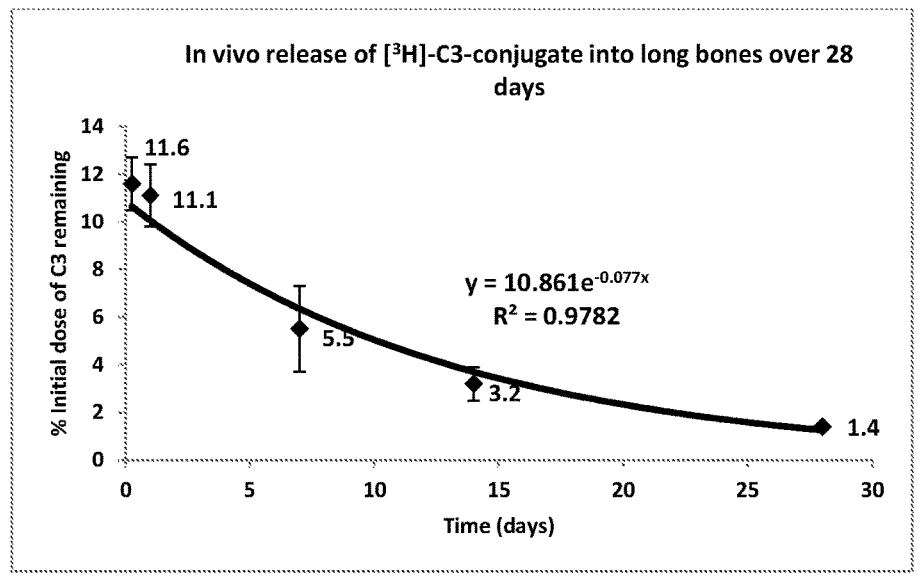
FIG. 11 is a graph showing the release of tritium-labelled C3-conjugates from rat long bones over 28 days.

The short-term study on the in vivo uptake of tritium-labelled C3-conjugate showed that 20% of the initial dose of conjugate was bound to bone 6 hours after injection. However the second study, a long-term study over 28 days, showed that ca. 12% of conjugate was taken up into bone at 6 hours (FIG. 11).

Figure 12:
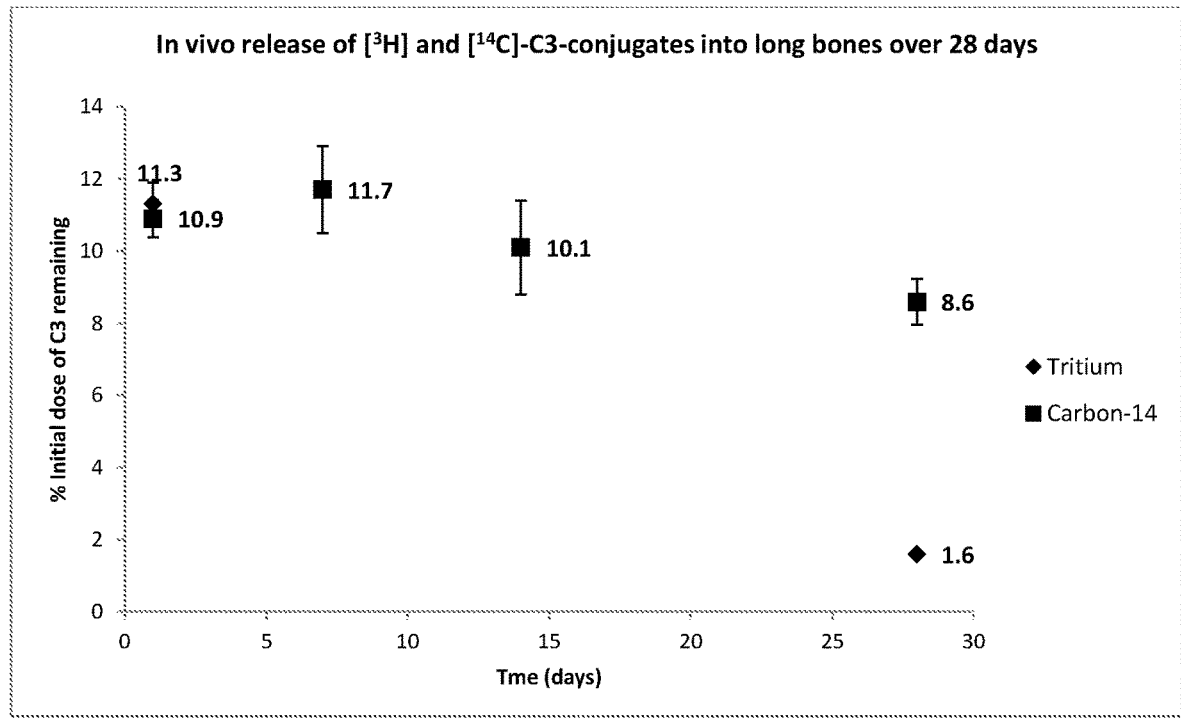
FIG. 12 is a graph showing the release of tritium and carbon-14-labelled C3-conjugates from rat long bones over 28 days.

The in vivo uptake and release study over 28 days using the double-radiolabelled compound confirmed these latter results (FIG. 12). Indeed both FIGS. 11 and 12 showed a slow release of the tritium label (EP4-agonist) with about 50% lost over 7 days. After 28 days, only 1.4% of the initial label remained attached to bone. 24 hours after dosing, about 11% uptake was observed for both labels. Unlike the tritium EP4-agonist which was slowly released, $^{14}C$-bisphosphonate-linker part remained bound to bone over 28 days (ca. 9-12%), indicating the lack of significant hydrolysis of the amide bond. A small but statistically insignificant loss of label was noticed at the 28 day time point but may be attributed to experimental variation or may reflect the actual intrinsic bone turnover rate (half-life of alendronate turnover is about 300 days) [Lin J H, Russell G, Gertz B. Pharmacokinetics of alendronate: an overview. Int J Clin Pract Suppl 1999; 101:18-26.].

Neutrophil Function Effects

Figure 13:
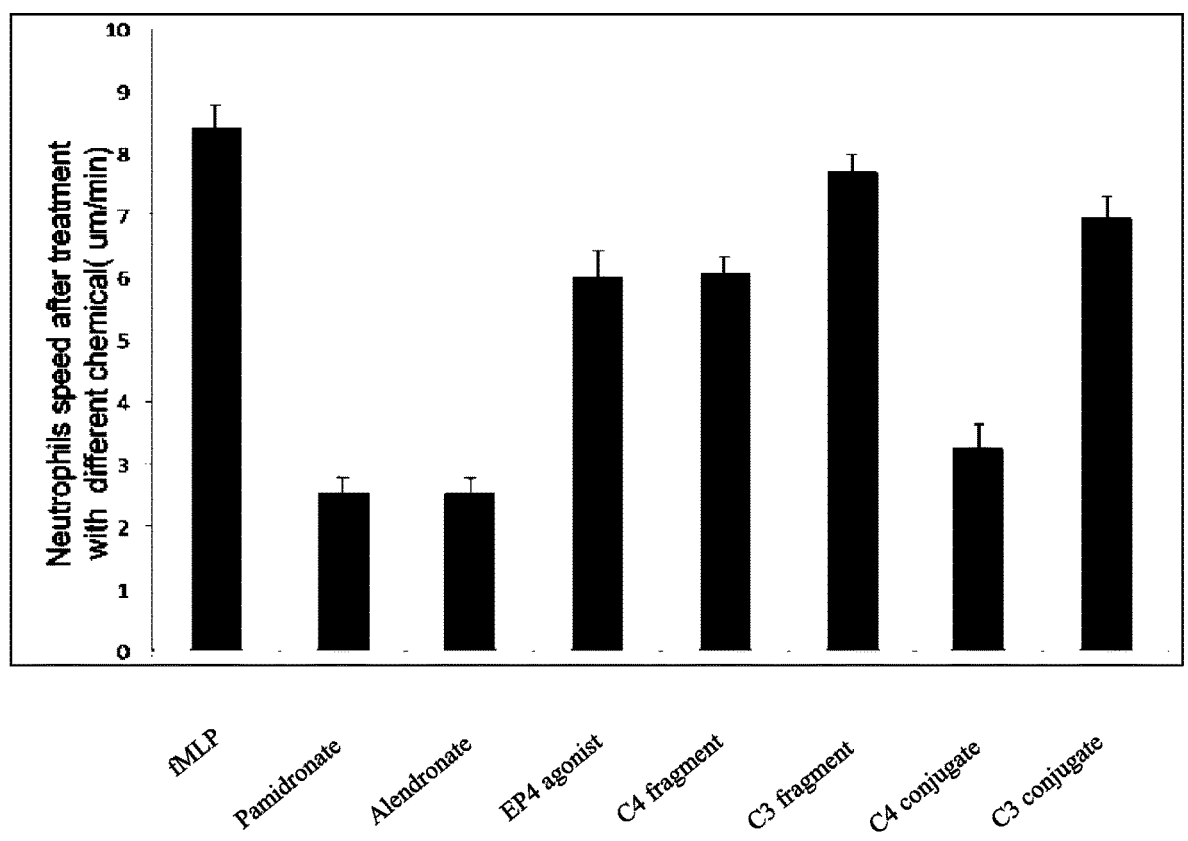
FIG. 13 is a graph showing neutrophil function effects of C3 and C4-conjugates and their respective fragments compared to EP4 agonist and bisphosphonates.

The neutrophil function effects of fragments 4 and 5 compared to their bisphosphonate moieties alone (alendronate and pamidronate, respectively), were evaluated. Compounds C3 (alendronate conjugate) and C4 (pamidronate conjugate), along with EP4 agonist, were also assayed. FIG. 13 shows that neither fragment 4 nor 5 exhibited significant activity in leukocytes, whereas alendronate and pamidronate were active. Furthermore, EP4 agonist and C3-conjugate exhibited a low neutrophil speed whereas C4-conjugate was active in leukocytes. The results obtained in vivo for the amide-linked conjugates displayed a higher bone-binding efficiency, compared to a carbamate-linked conjugate, as well as slower release of EP4 agonist. Moreover C3 fragment 4 containing the linker connected to alendronate, was biologically inactive compared to alendronate alone.

As used herein the singular forms "a", "and", and "the" include plural referents unless the context clearly dictates otherwise. For example, "a compound" refers to one or more of such compounds, and equivalents thereof as known to those skilled in the art.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A compound, or a pharmaceutically acceptable salt thereof, the compound comprising at least one EP4 agonist or related compound linked to an amide linker through an ester bond and an amino bisphosphonate linked to the amide linker through an amide bond, wherein the EP4 agonist or related compound is selected from

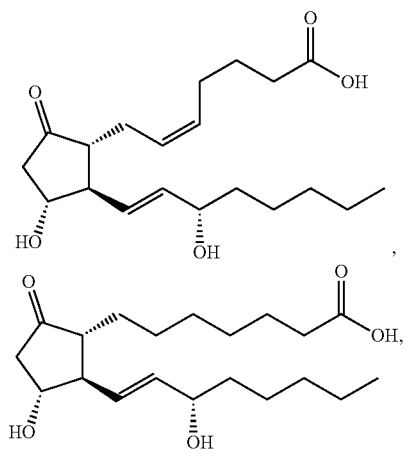

-continued

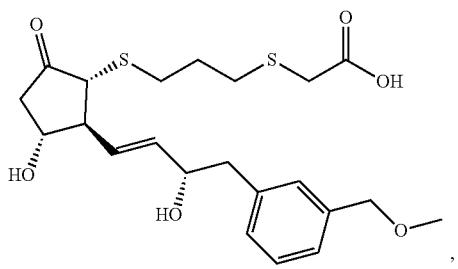

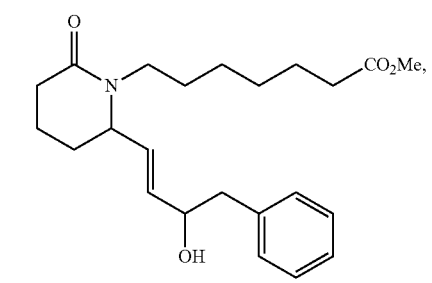

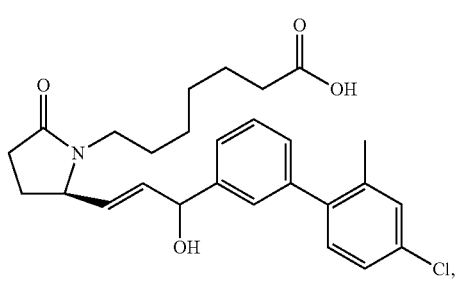

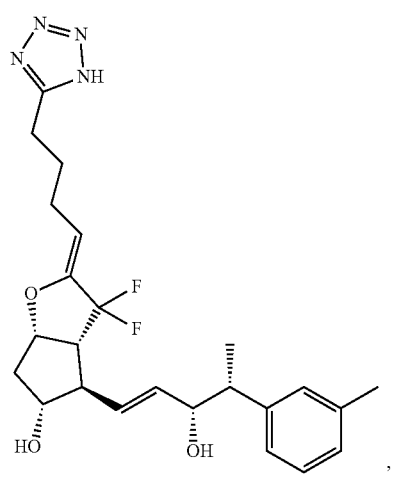

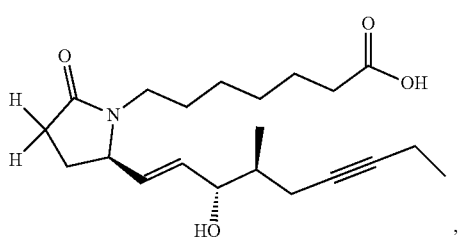

-continued

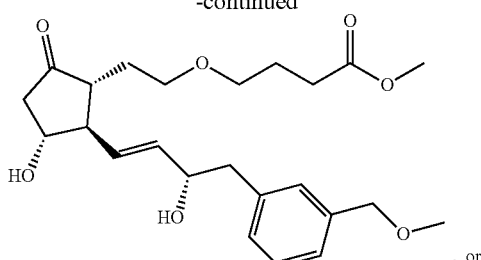

, or

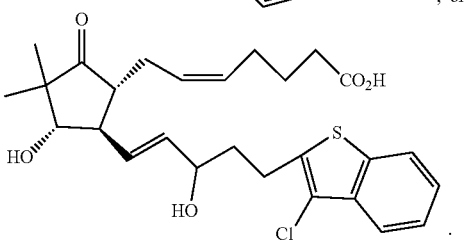

and wherein the amide linker comprises a structure selected from

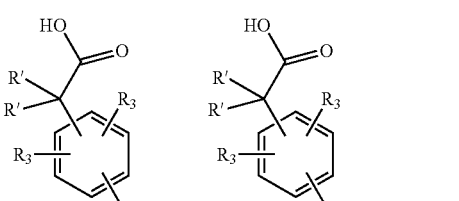

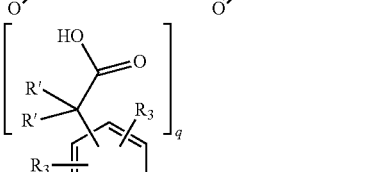

wherein
R3 is each independently H, OR', halogen, CN, or C(O)R',
R' is each independently H or alkyl with one to ten carbon atoms, or the two R's form a ring of up to 6 carbons,
NHR", if present, is the amino group of the amino bisphosphonate,
q, if present, is 1 or 2,
n, if present, is 1, 2 or 3,
and
wherein one or more of the aliphatic carboxylic acid groups can react with the C-15 hydroxyl group of the EP4 agonist or related compound, to form the ester bond, and the remaining carboxylic acid group can react with the amino group of the amino bisphosphonate to form the amide bond.

2. The compound of claim 1 wherein the compound is hydrolyzable in vivo.

3. The compound of claim 2 wherein the compound is inactive prior to hydrolyzation.

4. The compound of claim 1 wherein the amide bond is resistant to hydrolysis in vivo.

5. A pharmaceutical composition comprising the compound of claim 1, in combination with a pharmaceutically acceptable carrier.

6. A method of selectively delivering a compound to bone, the method comprising administering an effective amount of the compound of claim 1 to a subject in need thereof.

7. The method of claim 6 wherein the bone is a bone in need of treatment.

8. The method of claim 7 wherein the bone in need of treatment is selected from the group consisting of a green stick fracture, compound fracture, lateral fracture, pathologic fracture resulting from an invasive tumor, compression fracture, and fracture requiring a surgical procedure for realignment of a bone.

9. The method of claim 6 wherein the compound is hydrolyzed after binding to bone.

10. The method of claim 9 wherein the compound is inactive prior to hydrolyzation.

11. The method of claim 9 wherein the compound releases an active agent after hydrolyzation.

12. The method of claim 11 wherein the active agent is the EP4 agonist or related compound.

13. The method of claim 9 wherein the bisphosphonate moiety remains attached to the bone.

14. The method of claim 6 wherein the subject is a human.

15. A method of preparing a compound according to claim 1, comprising:
   i) providing at least one EP4 agonist or related moiety comprising a hydroxyl group, an amide linker comprising at least two carboxylic acid groups, and a bisphosphonate moiety comprising an amino group;
   ii) reacting one of the carboxylic acid groups of the amide linker with the hydroxyl group of the EP4 agonist or related moiety, to form an ester bond, and
   iii) reacting the other carboxylic acid of the amide linker group with the amino group of the bisphosphonate to form an amide bond.

16. The compound of claim 1 wherein the amide linker is 4-(carboxymethyl) benzoic acid or 3,5-bis-(carboxymethyl) benzoic acid.

17. The compound of claim 1 wherein the amino bisphosphonate has the following structure:

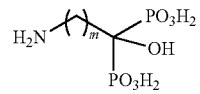

wherein m is 1, 2, 3, 4, 5 or 6.

18. The compound of claim 1 wherein the amino bisphosphonate is alendronic acid, 4-amino-1-hydroxybutylidene-1, 1-bisphosphonic acid; alendronate, 4-amino-1-hydroxybutylidene-1, 1-bisphosphonic acid monosodium trihydrate, 6-amino-1-hydroxyhexylidene-1, 1-bisphosphonic acid, or 3-amino-1-hydroxypropylidene-1, 1-bisphosphonic acid.

19. The compound of claim 1 wherein the EP4 agonist or related compound is

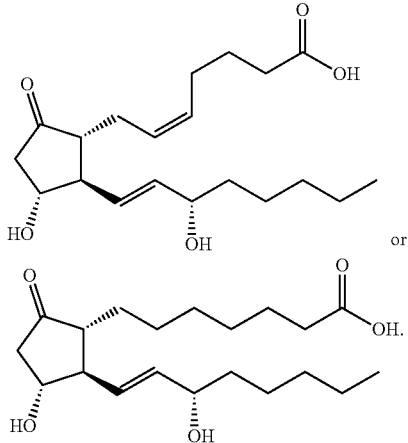

* * * * *